United States Patent
Chen et al.

(10) Patent No.: US 12,377,015 B1
(45) Date of Patent: Aug. 5, 2025

(54) SPERM EXTRACTOR AND STIMULATING DEVICE

(71) Applicant: Dongguan love angel electronic technology Co., LTD., Guangdong (CN)

(72) Inventors: Hao Chen, Guangdong (CN); QinDuo Wang, Guangdong (CN)

(73) Assignee: Dongguan love angel electronic technology Co., LTD., Guangdong (CN)

( * ) Notice: Subject to any disclaimer, the term of this patent is extended or adjusted under 35 U.S.C. 154(b) by 0 days.

(21) Appl. No.: 19/023,994

(22) Filed: Jan. 16, 2025

(30) Foreign Application Priority Data

Jan. 30, 2024 (CN) .......................... 202420234046.9
Dec. 11, 2024 (CN) .......................... 202423059306.2

(51) Int. Cl.
*A61H 19/00* (2006.01)
*A61B 10/00* (2006.01)

(52) U.S. Cl.
CPC ......... *A61H 19/32* (2013.01); *A61B 10/0058* (2013.01); *A61H 2201/1664* (2013.01); *A61H 2201/1692* (2013.01); *A61H 2205/087* (2013.01)

(58) Field of Classification Search
CPC ............ A61H 19/32; A61H 2201/1664; A61H 2201/1692; A61H 2205/087; A61B 10/0058

See application file for complete search history.

(56) References Cited

U.S. PATENT DOCUMENTS

| | | | | |
|---|---|---|---|---|
| 10,751,502 B2* | 8/2020 | Nishida | ............... | A61H 19/30 |
| 11,730,665 B1* | 8/2023 | Huang | ............... | A61H 23/02 |
| | | | | 600/38 |
| 11,737,949 B1* | 8/2023 | Huang | ............... | A61H 19/32 |
| | | | | 600/38 |
| 11,752,063 B1* | 9/2023 | Huang | ............... | A61H 19/32 |
| | | | | 600/38 |
| 11,896,542 B2* | 2/2024 | Sloan | ............... | A61H 7/005 |
| 11,925,592 B1* | 3/2024 | Huang | ............... | A61H 19/32 |
| 12,171,413 B2* | 12/2024 | Takahori | ............... | A61F 5/453 |
| 2017/0258456 A1* | 9/2017 | Wu | ............... | A61H 23/02 |
| 2021/0113424 A1* | 4/2021 | Yates | ............... | A61F 5/41 |
| 2021/0401409 A1* | 12/2021 | Nakamura | ......... | A61B 10/0058 |
| 2022/0168174 A1* | 6/2022 | Von Buttlar | ......... | A61H 19/32 |
| 2022/0323290 A1* | 10/2022 | Sloan | ............... | A61H 19/00 |

(Continued)

*Primary Examiner* — Guy K Townsend
(74) *Attorney, Agent, or Firm* — ScienBiziP, P.C.

(57) ABSTRACT

The present disclosure provides a sperm extractor, the sperm extractor may be a stimulation device, the sperm extractor including: a first massage member and a first driving mechanism, the first massage member including a first end, a second end opposite to the first end, and a lateral wall between the first end and the second end, the lateral wall surrounding and defining a first inserting space, the lateral wall including a first massage portion capable of massaging a glans of the penis received in the first inserting space; the first massage portion is driven to move by a motion of the connecting portion, the first massage portion is entirely deviating toward a first direction intersected with the inserting direction at a first moment and entirely deviating toward a second direction intersected with the inserting direction at a second moment, the first direction is different to the second direction.

20 Claims, 28 Drawing Sheets

(56) References Cited

U.S. PATENT DOCUMENTS

| | | | | |
|---|---|---|---|---|
| 2023/0072384 A1* | 3/2023 | Chen | ............ | A61H 23/02 |
| 2023/0083660 A1* | 3/2023 | Raju | ............ | A61H 19/32 |
| | | | | 600/38 |
| 2023/0126338 A1* | 4/2023 | Shao | ............ | A61H 15/0078 |
| | | | | 600/38 |
| 2024/0225950 A1* | 7/2024 | Liu | ............ | A61H 19/32 |

* cited by examiner

SPERM EXTRACTOR AND STIMULATING DEVICE

RELATED APPLICATIONS

This application claims the benefit of priority to Chinese Patent Application Number 202423059306.2 filed on Dec. 11, 2024, and Chinese Patent Application Number 202420234046.9 filed on Jan. 30, 2024, in the China National Intellectual Property Administration. The entire contents of the above-identified application are hereby incorporated by reference.

TECHNICAL FIELD

The present disclosure relates to the technical field of stimulating devices, and in particular, to a stimulating device for an extracting sperm.

BACKGROUND

In daily life and/or healthcare, it is often necessary to stimulate male and/or female reproductive systems to achieve treatments or improve quality of life. For example, reproductive centers, which are medical institutions specializing in reproductive health and fertility services, provide services such as diagnosis, treatment and counseling for infertile couples to help them solve their fertility problems. The quality of male sperms is an important factor for the fertility of couples. Sperm extractors are widely used for collecting semen samples. The stimulating device is an important portion of the sperm extractor for stimulating a penis to release sperm. Therefore, an improved stimulation device which is more conducive to stimulating a user's ejaculation is required.

BRIEF DESCRIPTION OF DRAWINGS

In order to illustrate the technical solution in embodiments of the present invention more clearly, the following briefly introduces accompanying drawings used in the description of the embodiments. Obviously, the accompanying drawings in the following description are only some embodiments of the present invention. Those of ordinary skill in the art can obtain other accompanying drawings from these accompanying drawings without any creative efforts.

DETAILED DESCRIPTION

Reference will now be made in detail to representative embodiments illustrated in the accompanying drawings. It should be understood that the following descriptions are not intended to limit the embodiments to one preferred implementation. To the contrary, the described embodiments are intended to cover alternatives, modifications, and equivalents as can be included within the spirit and scope of the disclosure and as defined by the appended claims.

First Embodiment

Figure 1:
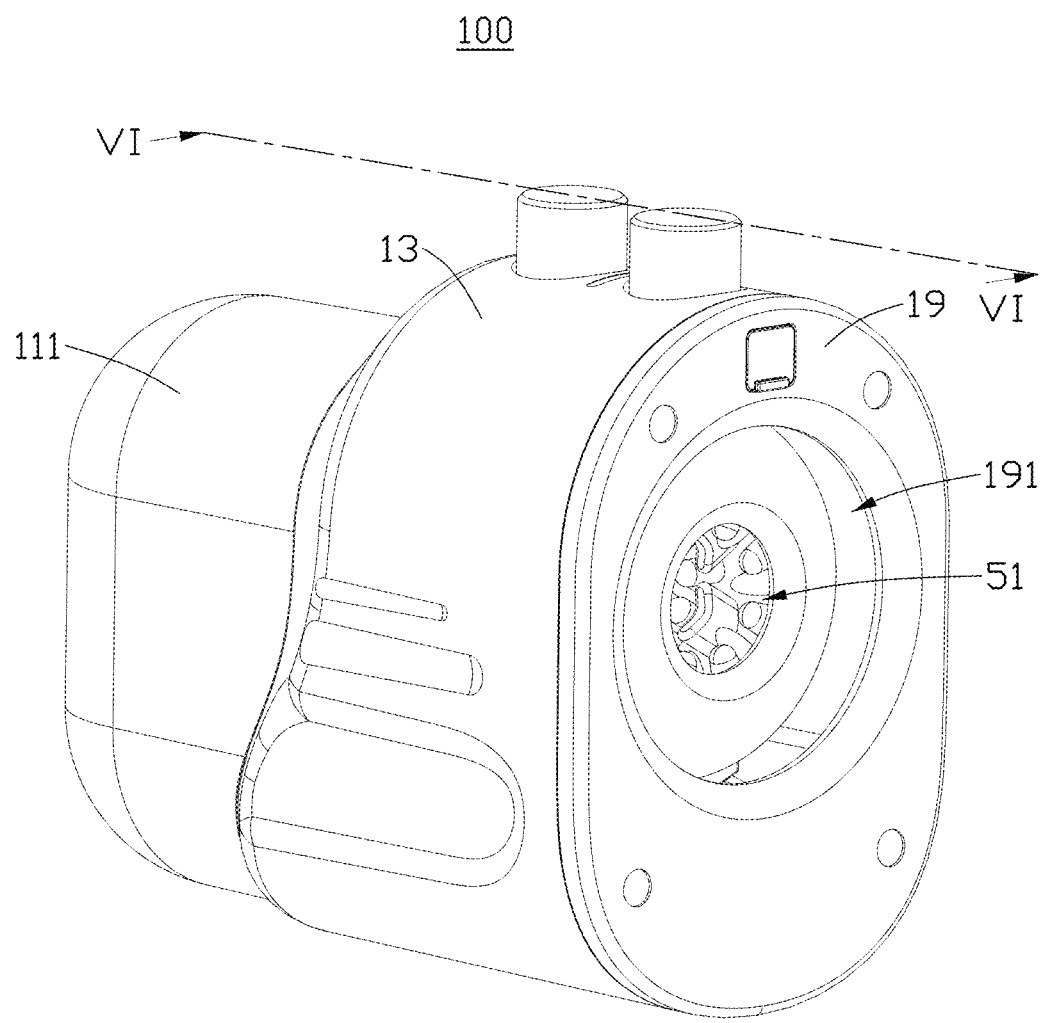
FIG. 1 is a perspective view of a sperm extractor according to a first embodiment of the present disclosure.
Figure 2:
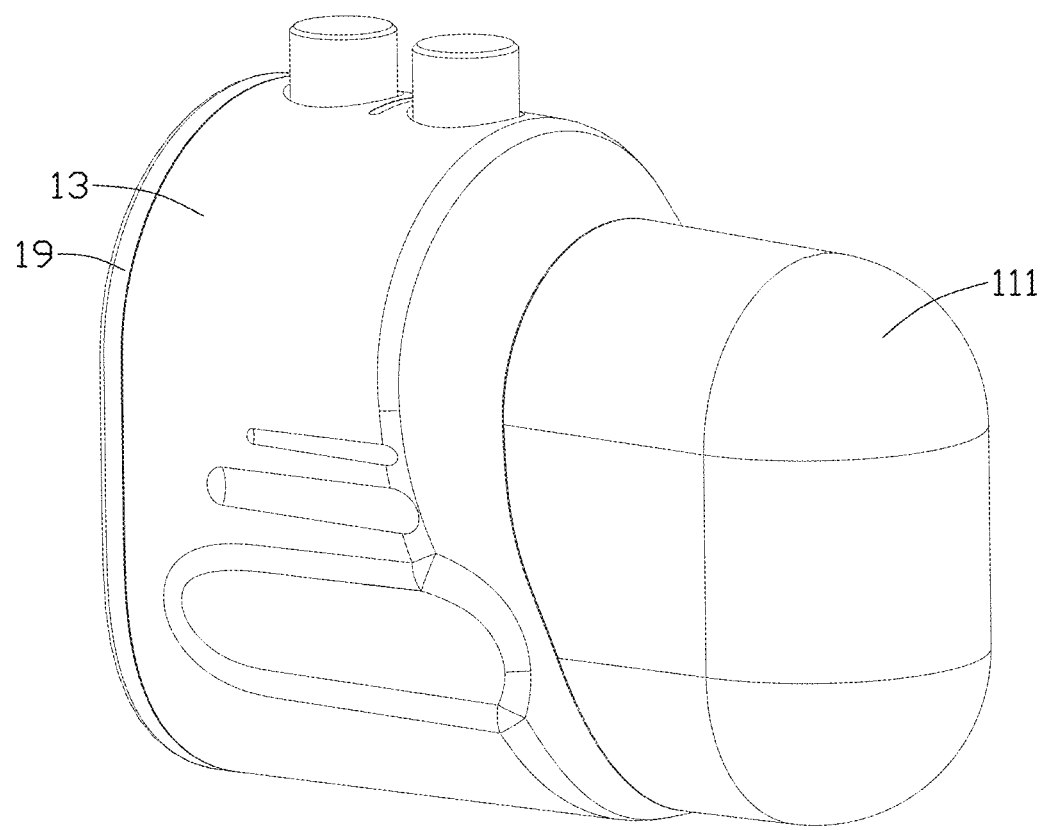
FIG. 2 is a perspective view of the sperm extractor shown in FIG. 1 showing from another view direction.

As shown in FIG. 1 and FIG. 2, a first embodiment of the present disclosure provides a sperm extractor 100 for collecting sperms of males. The sperm extractor may be a stimulating device which is capable of receiving at least a portion of penis, and stimulating the penis to secrete the sperms.

Refer to FIG. 1 to FIG. 3 and FIG. 6, the sperm extractor 100 comprises a housing 10, a power unit 80, a controller 90, a first massage module 105 and a second massage module 107. Each of the power unit 80 and the controller 90, the first massage module 105 and the second massage module 107 is received in the housing 10. The first massage module 105 and the second massage module 107 can engage different areas of a penis which is inserted into the housing 10. The first massage module 105 is configured for providing a first type of massage to the penis. The second massage module 105 is configured for providing a second type of massage to the penis. The first massage module 105 and the second massage module 107 are electrically coupled to the power unit 80 and the controller 90 so as to stimulate the penis with different movement modes. The different movement modes include swinging, shaking, vibration and the like. The power unit 80 is coupled to the controller 90 for providing electrical power.

The first massage module 105 and the second massage module 107 are disposed along an inserting direction along which the penis is inserted. The first massage module 105 comprises a first massage member 40 for massaging a first area of the penis and a first driving mechanism 20 for driving the first massage member 40. The second massage module 107 comprises a second massage member 60 for massaging a second area of the penis and a second driving mechanism 30 driving the second massage member 60. A receiving space 101 is defined in the housing 10 to receive the power unit 80, the controller 90, the first driving mechanism 20, the first massage member 40, the second driving mechanism 30 and the second massage member 60 therein. The first massage member 40 and the second massage member 60 are arranged side by side along an arrangement line (parallel to the X direction), and cooperatively define an inserting space 50, the inserting space 50 is configured for receiving at least a portion of the penis. The inserting space 50 is extended along the inserting direction. Specifically, the first massage member 40 and the second massage member 60 are different portions of a single element. The second massage member 60 includes an opening 51 at an end which is away from the first massage member 40. The arrangement line extends through the opening 51. The opening 51 is air communicated with the inserting space 50, so that the penis is capable of inserting into the inserting space 50 through the opening 51. A glans portion of the penis is insertable into the first massage member 40 after inserting through the second massage member 60, so that the glans portion can be stimulated by the first massage member 40 under the driving of the first driving mechanism 20 using the first type of massage, and at least a middle portion of the penis can be stimulated by the second massage member 60 under the driving of the second driving mechanism 30 using the second type of massage.

The housing 10 may comprise a first housing 11, a second housing 13 and a shell 111. The first housing 11 and the second housing 13 are arranged side by side along the arrangement line, and the first housing 11 is connected to the lower portion of the second housing 13 together. The shell 111 entirely covers the first housing 11 and engages with the second housing 13. A first portion of the receiving space 101 is defined by a cooperation of the first housing 11 and the shell 111, and a second portion of the receiving space 101 is defined by the second housing 13. The first driving mechanism 20 is partly received in the first portion of the receiving space 101, and the power unit 80, the controller 90, the second driving mechanism 30, and the second massage member 60 are received in the second portion of the receiving space 101.

Figure 4:
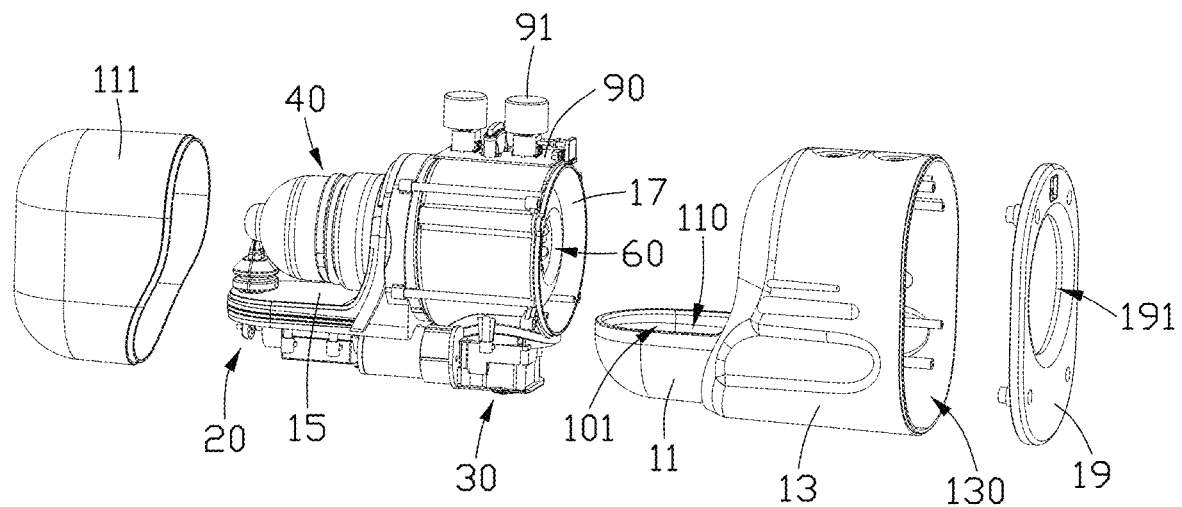
FIG. 4 is a perspective view of the sperm extractor shown in FIG. 1 with both of the shell and a second housing removed.

As shown in FIG. 4, a recess 110 is defined in a top side of the first housing 11. The first driving mechanism 20 is received in the recess 110. The first massage member 40 is disposed above the first housing 11, and the first driving mechanism 20 extends out of the recess 110 to engage with the first massage member 40, so as to drive the first massage member 40 to move. The first driving mechanism 20 includes a first connecting member 201 configured for connecting with the first massage member 40. The first connecting member 201 has a small connecting area with the first massage member 40. The small connecting area may be smaller than 1/10 of the size of the first massage member 40, especially functions as a point. A channel 130 is defined to penetrate through the second housing 13 along the inserting direction, and air communicated with the recess 110 and the receiving space 101. A cover 19 is detachably installed on a distal end of the second housing 13 which is away from the first housing 11. An opening hole 191 is defined in the cover 19, and the opening hole 191, the channel 130 and the opening 51 are co-axial along the inserting direction and air communicated to each other.

Figure 5:
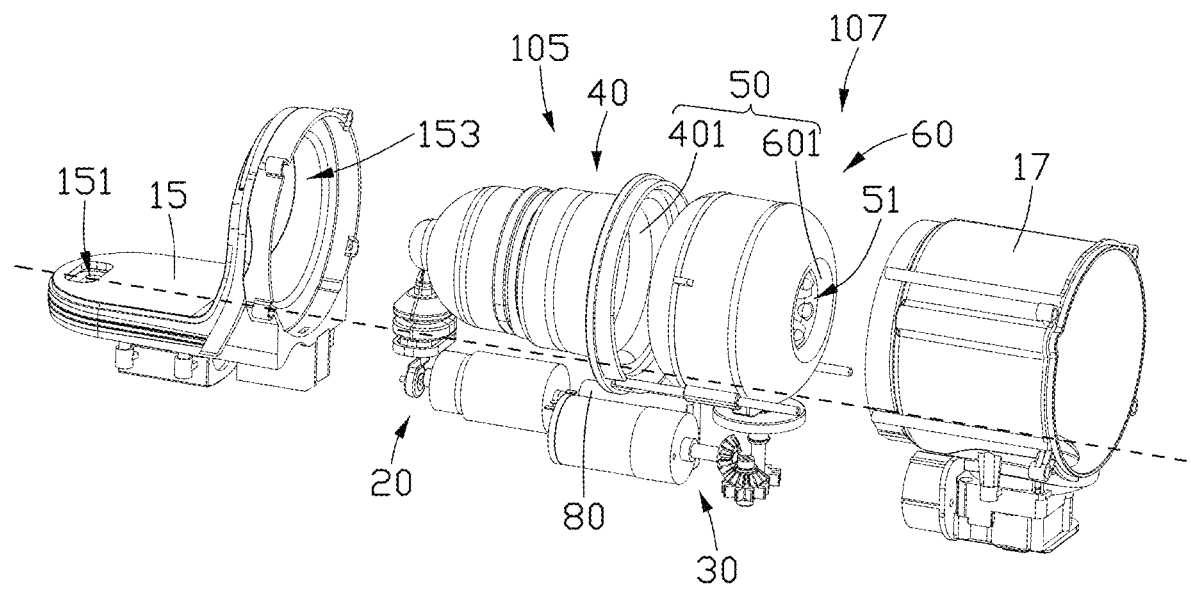
FIG. 5 is a perspective view of the sperm extractor shown in FIG. 4 with a first support plate and a tube removed.
Figure 6:
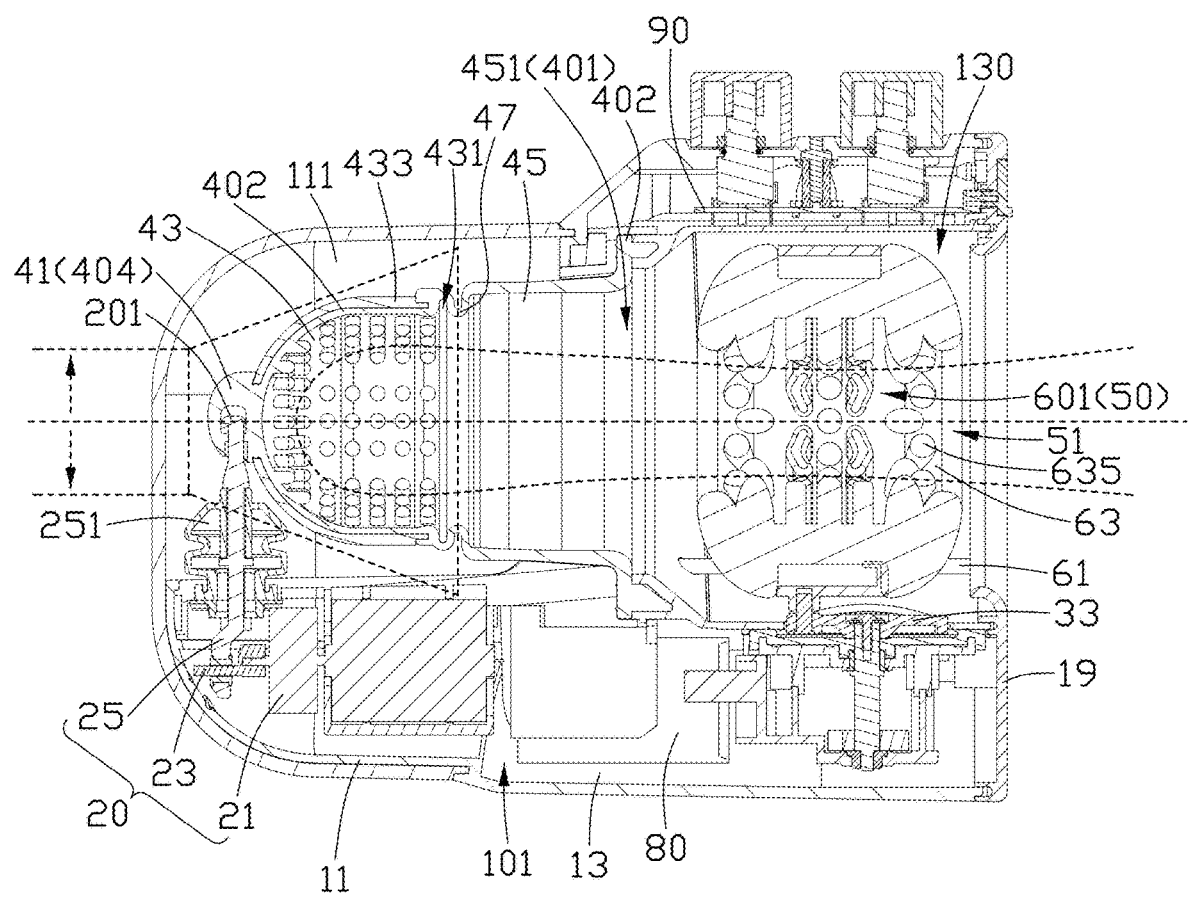
FIG. 6 is a cross-sectional view along a VI-VI direction of the sperm extractor shown in FIG. 1.

As shown in FIG. 5 and FIG. 6, a first support plate 15 is fixedly installed on the top of the first housing 11. The first support plate 15 is undeformable, while the first massage member 40 is deformable. The first support plate 15 may include a main plate covering the recess 110 and a mounting ring 153 perpendicularly extending from a side of the main plate. A first hole 151 is defined in the first support plate 15 opposite to the first driving mechanism 20, so that the first driving mechanism 20 can pass through the first hole 151 and engage with the first massage member 40. The first massage member 40 is disposed on the main plate with one end of the first massage member 40 being inserted into the mounting ring 153. A tube 17 is connected to the mounting ring 153 of the first support plate 15, the tube 17 is a cylindrical hollow structure for receiving the second massage member 60 and is received in the second housing 13.

The controller 90 is disposed on the tube 17, with two buttons 91 on the controller protruding out of the second housing 13. One of two buttons is used to activate the first driving mechanism 20, and the other is used to activate the second driving mechanism 30.

The shell 111 is detachably attached to a side of the second housing 13 opposite to the cover 19. The first massage member 40 is received in the shell 111, so that the first massage member 40 is protected from dust. It can be understood that the shell 111 can be fixedly connected with the second housing 13 to form a housing 10. The penis is insertable into the first massage member 40 and the second massage member 60 from the opening hole 191 of the cover 19.

Furthermore, a portion of the shell 111 corresponding to the first massage member 40 is transparent, allowing the moving direction of the first massage member 40 to be visualized by the users.

Refer to FIG. 5 and FIG. 6, the first driving mechanism 20 is mainly received in the recess 110 of the first housing 11, and a portion of the first driving mechanism 20 is protruded from the first hole 151 and engaged with the first massage member 40. The first driving mechanism 20 includes a first driving source 21, a first wheel 23, and a first rod 25. The first driving source 21 may be a motor which is received in the recess 110. The first driving source 21 includes a shaft extending along a first direction which is parallel to the inserting direction. The shaft is rotatable when driven by the first driving source 21. The shaft of the first driving source 21 is fixedly coupled to the first wheel 23 which is received in the recess 110, and the first wheel 23 is eccentrically connected to the first rod 25. One end of the first rod 25 is fixedly connected with the first wheel 23, and the other end of the first rod 25 is extended passing through the first hole 151 and coupled to the first massage member 40. The first rod 25 is disposed to extend along a second direction which is perpendicular to the first direction (e.g. Y direction), so as to move up and down along the Y direction when the shaft rotates. The connecting area of the first rod 25 and the first massage member 40 may be located at a distal end of the first massage member 40 in the X direction. The distal end of the first massage member 40 is pushed up and pull down by the first rod 25 so that at least of most of the first massage member 40 is driven to swing up and down. The swing of the most of the first massage member 40 can massage the penis and achieve the first type of massage. In this embodiment, the shaft of the motor is connected to one center end of the first wheel 23.

As shown in FIG. 5, a portion of the first rod 25 protruding out of the first housing 11 is sleeved by a sleeve 251, and the sleeve 251 is made of a silica gel material and formed into a stacked pleat shape, so as to achieve a waterproof effect.

Refer to FIG. 6, the first massage member 40 is disposed with extending along the X direction. A first end 403 of the first massage member 40 is fixed to an inner wall of the mounting ring 153, and a second end 404 is coupled to a top end of the first rod 25. The first end 403 and the second end 404 are opposite ends of the first massage member 40 in the X direction, a lateral wall 402 located between the first end 403 and the second end 404. In this embodiment, the first massage member 40 is generally hollow-shaped for defining a first inserting space 401, which is a portion of the inserting space 50. The first inserting space 401 is extended along the X direction. The first massage member 40 further defines a second opening 451, which is air communicated with the first inserting space 401 and faces the second massage member 60, in the first end 403. The second end 404 is a closed end which cooperates with the lateral wall 402 to define the first inserting space 401.

A connecting portion 41 is formed at the second end 404 of the first massage member 40 for connecting with the first driving mechanism 20. An first massage area 43 and a second massage area 45 are defined in the first inserting space 401. The first massage area 43 is located to adjacent to the second end 404 of the first massage member 40, while the second massage area 45 is adjacent to the first end 403 of the first massage member 40. The first massage area 43 may have a similar length as the second massage area 45 in the X direction.

Figure 7:
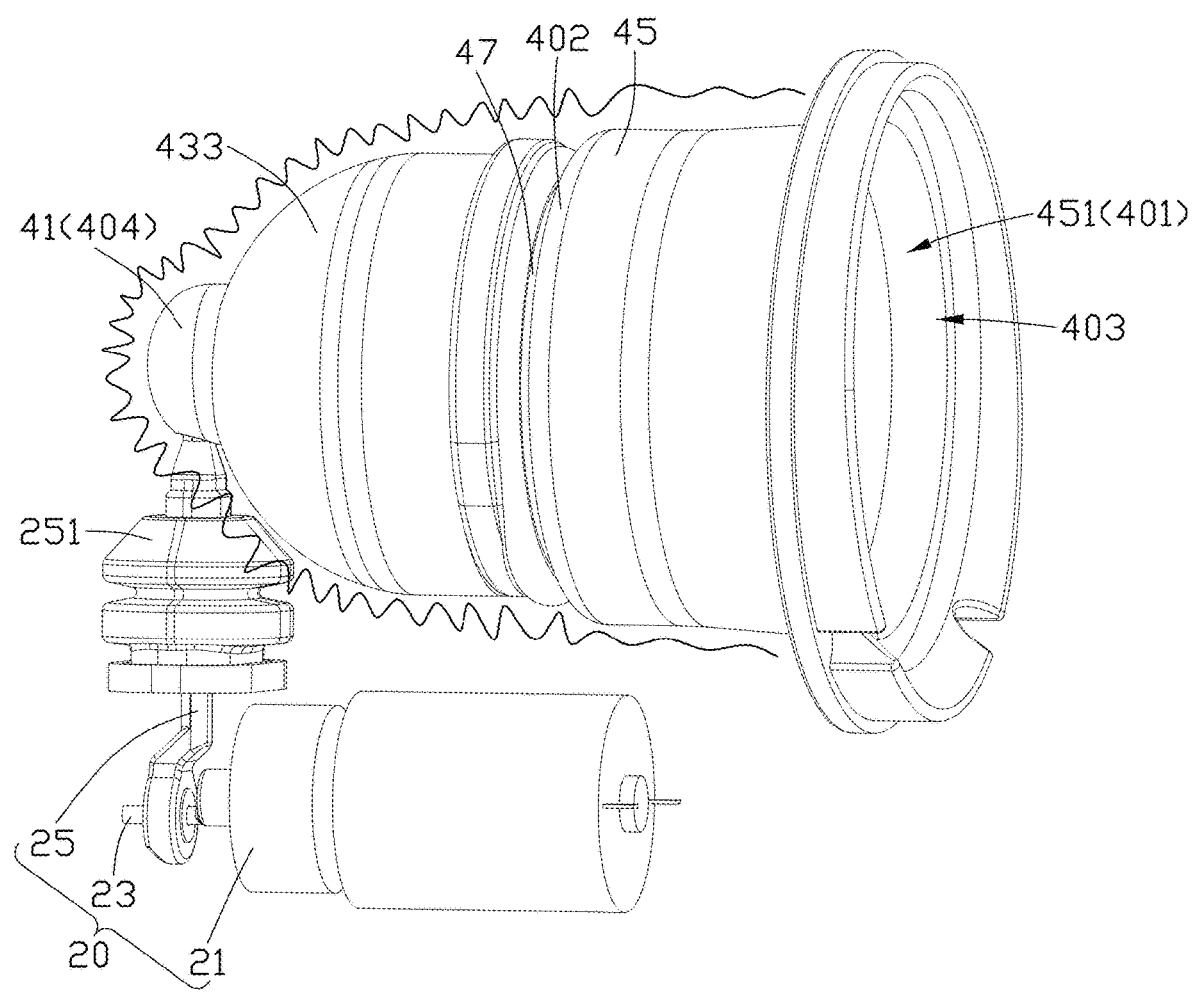
FIG. 7 is a view showing an assembly of a first driving mechanism and a first massage member.

Refer to FIG. 5 to FIG. 7, the connecting portion 41 has a closed hemispherical shape, and the top end of the first rod 25 away from the first wheel 23 engages with the connecting portion 41, so that the connection portion 41 is driven to do the reciprocating motion at a direction perpendicular to the X direction, the second end 404 and the lateral wall 402 of the first massage member 40 swing along the X direction together with the reciprocating motion of the connecting portion 41. The swing motion stimulates the glans and the portion of the penis in the first inserting space 401 to secret the sperms. The connecting portion 41 is made of a first material which has large elasticity, such as silicone material.

Figure 3:
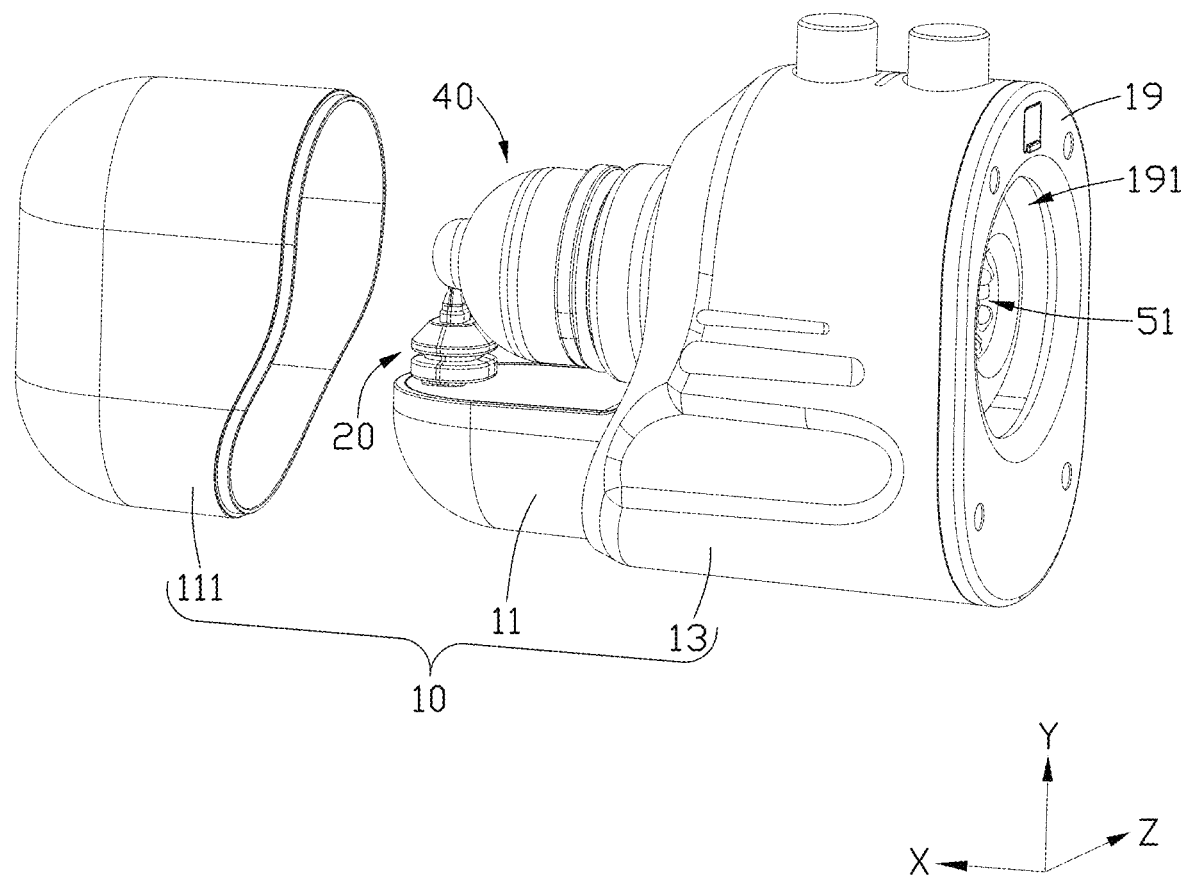
FIG. 3 is a perspective view of a portion of the sperm extractor shown in FIG. 1 with a shell removed.

Refer to FIG. 3 and FIG. 7, the first massage area 43 is accommodated between the second massage area 45 and the connecting portion 41. The first massage area 43 has a hollow structure with one end closed by the connecting portion 41 and the other end connected to the second massage area 45. A first opening 431 is defined at an end of the first massage area 43 adjacent to the second massage area 45. The first massage area 43 is substantially funnel-shaped, and the cross-sectional area along the X direction gradually increases from the side close to the connecting portion 41 to the side away from the connecting portion 41. A plurality of protrusions configured for contacting with the penis are protruded from an inner surface of the lateral wall 402 at the first massage area 43, in other words, the first massage area 43 may be an enhanced massage area which is capable of contacting with the penis quickly and enhancing the stimulation to the penis, while the second massage area 45 may be a non-enhanced massage area.

An outer surface of the lateral wall 402 at the first massage area 43 is surrounded by a first sleeve 433 for preventing the first massage area 43 from sagging due to gravity, and the first sleeve 433 is made of a second material which has small elasticity, such as a plastic hard shell and the like, the elasticity of the second material is smaller than that of the first material. The first massage member 40 is extendable easily in the X direction under the support of the first sleeve 433. When the connecting portion 41 is driven to move by the first rod 25, the first massage area 43 experiences a higher massage intensity, and the penis receives a relatively intense massage force, and the second massage area 45 is driven to move synchronously by the first massage area 43.

In some other embodiments, the sleeve 251 may be made of a first material which has a large elasticity, and the shell 111 is made of a second material with a smaller elasticity. The first massage member 40 is made of a third material, and the elasticity of the third material is between that of the first material and that of the second material.

One end of the second massage area 45 is engaged with the first massage area 43, and the other end is fastened on the inner wall of the mounting ring 153. Both ends of the second massage area 45 include second openings 451, the second openings 451 are air communicated with the first opening 431 and cooperatively to form the first inserting space 401. The penis is inserted into the first inserting 401 from the mounting ring 153 through the second opening 451, and performs massage to rapidly produce the sperms.

The second massage area 45 is made of the first material, and a buffer portion 47 is formed at one end of the second massage area 45 near the first massage area 43, the buffer portion 47 has a good elastic force and serves as a main stress position of the second massage area 45. On one hand, the buffer portion 47 moves under the drive of the connecting portion 41, and on the other hand, the buffer portion 47 is prevented from being separated from the mounting ring 153 due to an excessive friction between the second massage area 45 and the mounting ring 153 when the second massage area 45 moves. In this embodiment, the buffer portion 47 is a wrinkle.

In this embodiment, the connecting portion 41, the first massage area 43 of the lateral wall 402 and the second massage area 45 of the lateral wall 402 are made of the first material, with the first massage area 43 being covered with the first sleeve 433 which made of the second material. One end of the first massage member 40 is fixedly connected to the mounting ring 153, and the first massage member 40 extends along the X direction and is arranged in parallel with the first housing 11 at an interval. The other end of the first massage member 40 is connected with the first rod 25, so that the first massage member 40 is supported by the first rod 25. Therefore, when the penis is inserted into the first inserting space 401, the penis is stably supported by the first sleeve 433, and one end of the first rod 25 near the first wheel 23 moves up and down under the drive of the first driving mechanism 20, the other end of that drives the connecting portion 41 to move simultaneously.

Since the connecting portion 41 is only supported by the first rod 25, and the connecting portion 41 is made of the first material which has a large elasticity, when the first rod 25 is driven to move up and down at a high frequency, the connecting portion 41 drives the first massage area 43 of the lateral wall 402 to do a irregularly motion. The track of the motion is not linear, that is, the movement direction of the first massage member 40 comprises an up-and-down direction, a left-and-right direction. Will the connecting portion 41 swings with a first scale, the lateral wall 402 may shake with a second scale which is much smaller than the first scale due to the elasticity and inertial force of the first material. In other words, the first massage member 40 swings up and down and elastically shakes at left and right directions simultaneously or along a clockwise or counterclockwise direction.

The connecting portion 41 drives the lateral wall 402 to swing up and down so as to massage the penis, when the first rod 25 continues to move up and down. the connecting portion 41 is not only driven by the first rod 25, but also receives the elastic force and the inertia force of the first massage member 40, so that the connecting portion 41 moves in a linear movement and a rotational movement, and movement effects include shaking, vibration, swing, rotation and so on. Therefore, the penis is subjected to the massage motion in the directions of shaking, vibration, swing, rotation, and the like, and the massage force of the first massage area 43 is strong relative to the second massage area 45.

Figure 8:
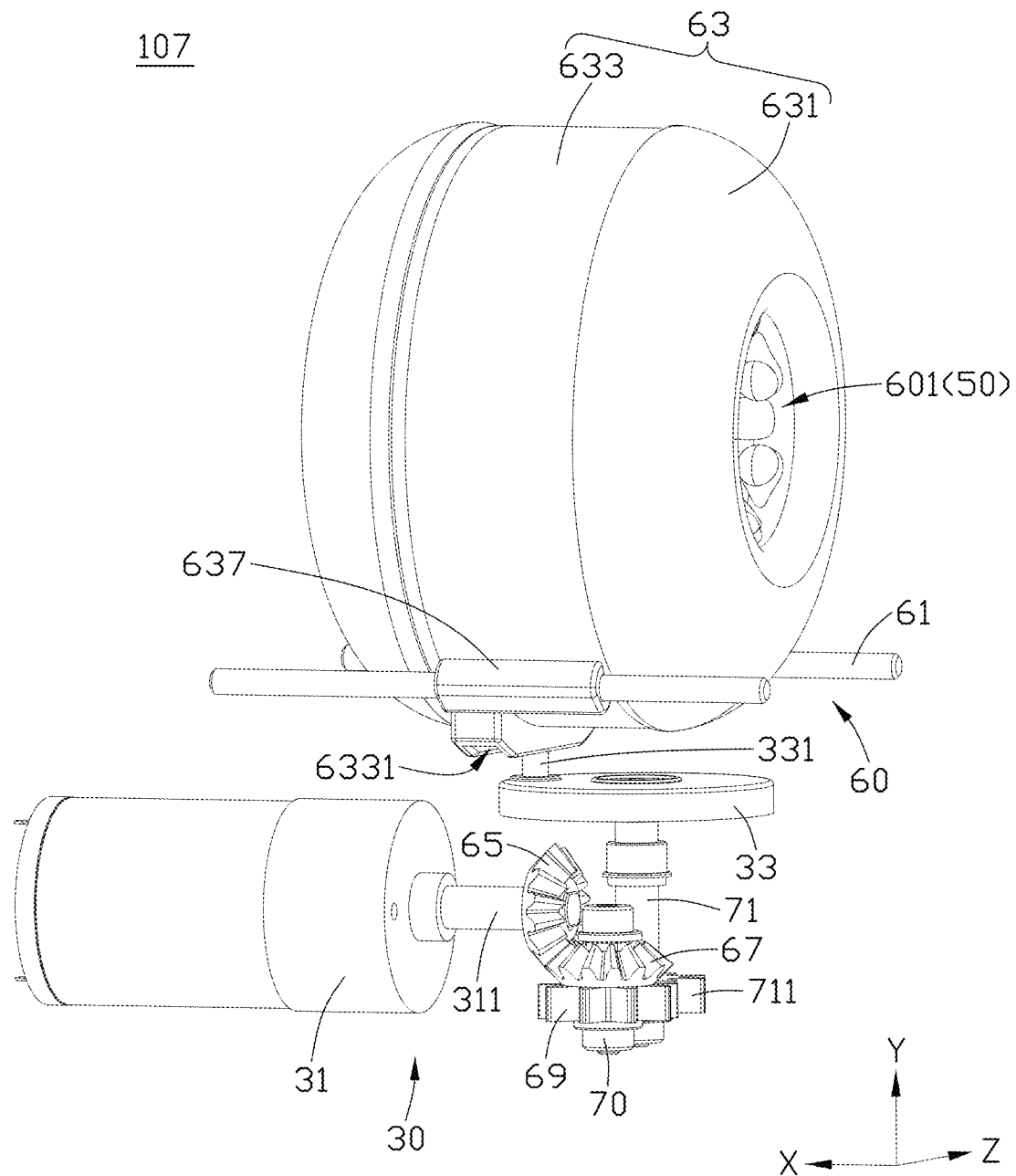
FIG. 8 is a view showing a second driving mechanism engaging with a second massage member.
Figure 9:
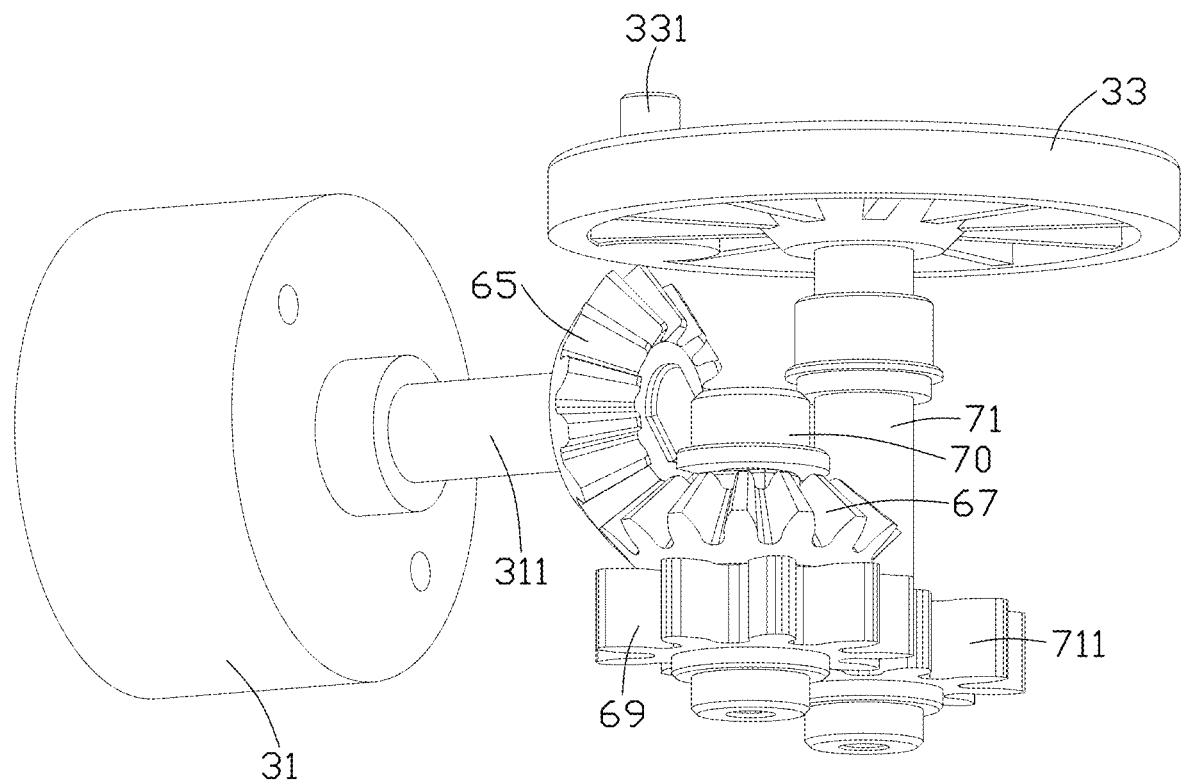
FIG. 9 is an enlarged view of a meshing mechanism shown in FIG. 8.

As shown in FIG. 8, the second massage module 107 comprises a second driving mechanism 30 and a second massage member 60. Under the drive of the second driving mechanism 30, the second massage member 60 is driven to slide along the X direction 13.

The second driving mechanism 30 is received in the second housing 13 (referring to FIG. 6). The driving mechanism 30 comprises a driving member 31 and a rotating member 33. An output shaft 311 is extended from an end of the driving member 31. One end of the rotating member 33 engages with the second massage member 60 so that the second massage member 60 is driven to do motions, the other end of that is meshing with the output shaft 311.

One end of the output shaft 311 is connected to a first meshing member 65, which is a bevel gear. A fixed post 70 is disposed adjacent to the first meshing member 65. The fixed post 70 is fixedly installed in the second housing 13 and is arranged perpendicular to the first meshing member 65. A second meshing member 67 and A third meshing member 69 are wound along the Y direction and rotatably installed onto the fixed post 70. The end of the second meshing member 67 and the end of the third meshing member 69 are engaged, thereby allowing the third meshing member 69 to rotate simultaneously when the second meshing member 67 rotates.

A mounting pole 71 is disposed adjacent to the fixed post 70. The mounting pole 71 is rotatably installed in the second housing 22. A fourth meshing member 711 is connected to the outer surface of the mounting pole 71. When the fourth meshing member 711 rotates, it synchronously drives the mounting pole 71 to rotate. In this embodiment, the fourth meshing member 711 is a cylindrical gear which is compatible with the third meshing member 69, that is to say, the third meshing member 69 meshes with the fourth meshing member 711. When the third meshing member 69 rotates, it synchronously drives the fourth meshing member 711 to rotate, the fourth meshing member 711 then drives the mounting pole 71 to rotate. A rotating member 33 is connected to one end of the mounting pole 71. When the mounting pole 71 rotates, it drives the rotating member 33 to rotate, the rotating member 33 then drives the second massage member 60 to move reciprocally along the X direction.

When the fourth meshing member 711 is rotated by the drive of the third meshing member 69, the mounting pole 71 connected to the fourth meshing member 711 is driven to rotate. Simultaneously, the rotating member 33 on the mounting pole 71 take to rotate together, then drives the second massage member 60 to slide. In detail, under the drive of the driving member 31, the output shaft 311 drives the first meshing member 65 to rotate. The second meshing member 67, which meshes with the first meshing member 65, also rotates. Driven by the second meshing member 67, the third meshing member 69 connected to the end of the second meshing member 67 rotates synchronously. The fourth meshing member 711, which meshes with the third meshing member 69, also rotates accordingly. Since the fourth meshing member 711 is connected to the mounting pole 71, when the fourth meshing member 711 rotates, the erection column 71 rotates synchronously. The rotating member 33 is connected to one end of the mounting pole 71, and as the mounting pole 71 rotates, the rotating member 33 also rotates, thereby providing the driving force for the second massage member 60.

Figure 10:
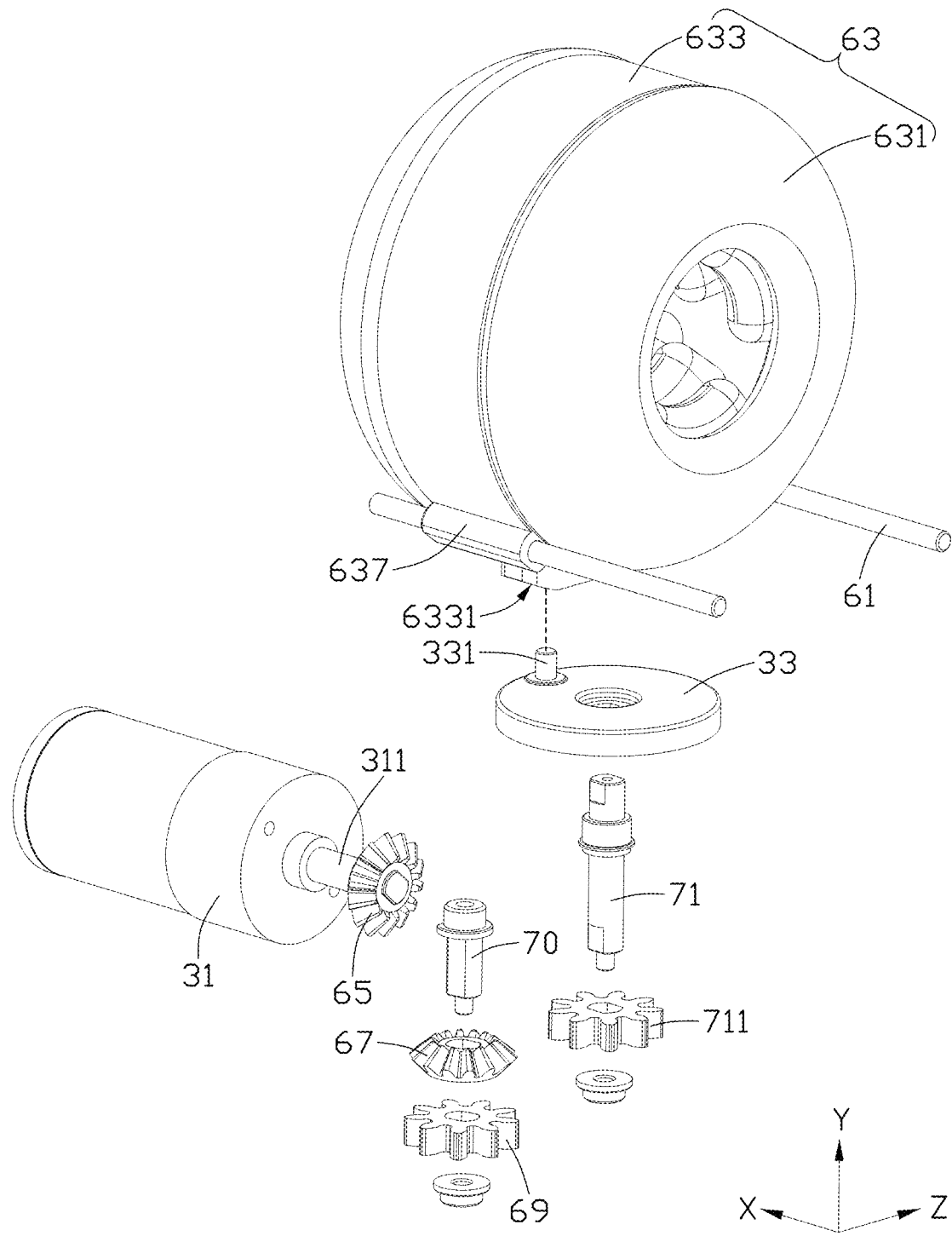
FIG. 10 is an exploded view of the meshing mechanism shown in FIG. 9.

As shown in FIG. 10, the second massage member 60 is accommodated in the second housing 13. The second massage member 60 comprises a sliding guide 61 and a massage piece 63 slidably arranged on the sliding guide 61. The sliding guide 61 is configured to extend along the X direction which is parallel to the insertion direction of the penis, and two ends of the sliding guide 61 is fixedly connected to the cover 19 and the end of the massage cylinder 45 (referring also to FIG. 3). A second rod 331 is protruded from a location which is distant from the center of the rotating member 33 at the side near the massage piece 63, the massage piece 63 is movably connected to the sliding rod 61, so that the rotation of the rotating member 33 is converted to move along the length direction of the sliding member 61.

The massage piece 63 is accommodated in the fixing housing 17. The massage piece 63 comprises a receiving portion 631 and a connecting member 633. In this embodiment, the receiving portion 631 is a cylindrical hollow structure with a second inserting space 601. The second inserting space 601 is a portion of the inserting space 50. The connecting member 633 surrounds the middle of the outer circumference of the receiving portion 631. The receiving portion 631 is made of the first material than that of the connecting member 633. At least one protrusion 635 is projected from the inner wall of the second inserting space 601 inwardly. In this embodiment, there are several protrusions 635 surrounding the inner wall of the massage piece 63 that are in contact with the penis, thereby further enhancing the massage effect. The second inserting space 601 is air communicated with the channel 130 (refer also to FIG. 4) and the opening hole 191. The side of the second inserting space 601 opposite to the first inserting space 401 corresponds to the opening 51. That is, the second inserting space 601, the opening 51, and the channel 130 are air communicated with each other and arranged along the X direction. The pathway for the penis comprises the opening hole 191, the second inserting space 601, the second opening 451, and the first inserting space 401.

The connecting member 633 is fixedly accommodated in the outer wall of the receiving portion 631. The connecting member 633 is slidably connected to the sliding guide 61. Under the drive of the driving member 31, the connecting member 633 slides along the sliding guide 61, so that the receiving portion 631 moves forwardly and backwardly in the second housing 13.

A connecting shaft 637 is protruded from the outer circumference of the connecting member 633. The connecting shaft 637 is capable of sliding along the sliding guide 61. A sliding groove 6331 is protrusively defined in the bottom of the connecting member 633 near the second rod 331. The sliding groove 6331 is a strip shape along the direction perpendicular to the length of the sliding guide 61, e.g. the Y direction. The second rod 331 is fixed to the connecting member 633 in the Z direction. The second rod 331 is inserted into the sliding groove 6331 and slidable along the sliding groove 6331 in the Y direction. Therefore, when the driving member 31 rotates, the output shaft 311 drives the rotating member 33 to rotate, the second rod 331 is driven to move along the sliding groove 6331 in the Y direction, the connecting member 633 is then driven to slide in the sliding rod 61, thereby achieving the forward and backward reciprocal sliding motions of the second massage member 60 in the X direction driven by the second driving mechanism 30.

When using the sperm extractor 100, the penis is inserted into the inserting space 50, and the pathway for the penis comprises the opening hole 191, the channel 130, the second inserting space 601, the second opening 451, the first inserting space 401. When one of the control buttons 91 is enabled, the first driving mechanism 20 is started to work, and the first wheel 23 is driven to rotate by the first driving source 21, and the first rod 25 is driven to move up and down by the first wheel 23, and then the connecting portion 41 drives the lateral wall 402 to move in a curved track, performing irregular motions including swing, shaking, and rotation. When the other control button 91 is enabled, the output shaft 311 is driven to rotate by the driving member 31 and drives the rotating member 33 to slide in the sliding groove 6331, so that the connecting member 633 is driven to slide on the sliding rod 61, and the penis is massaged by the sliding movement and rapidly produces sperm under the massage stimulation.

Second Embodiment

Figure 11:
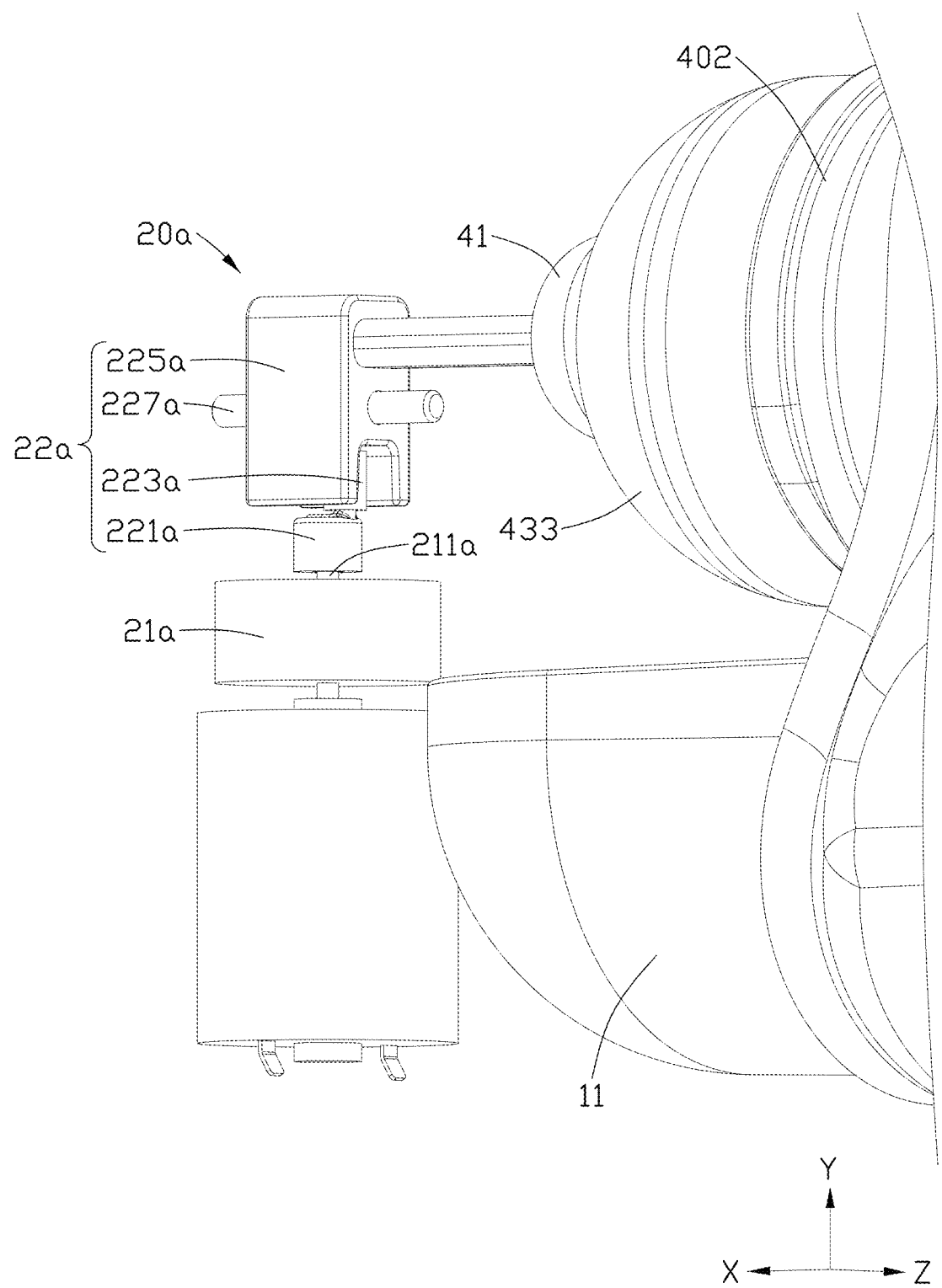
FIG. 11 is a partial perspective view showing a first driving mechanism of a sperm extractor according to a second embodiment of the present disclosure.

As shown in FIG. 11, reference numerals same as those in Embodiment 1 continue to be used for same elements in this embodiment. A difference between this embodiment and Embodiment 1 lies in the structure of the first driving mechanism 20a.

The first driving mechanism 20a in this embodiment includes a first driving source 21a, a first output shaft 211a, and a transmission member 22a. One end of the transmission member 22a is connected to a center of the connecting portion 41, and the other end is connected to the first driving source 21a through the first output shaft 211a. The first driving source 21a drives the first output shaft 211a to rotate along the Y direction, the first output shaft 211a drives the transmission member 22a to move, and the transmission member 22a drives the connecting portion 41 to swing along Z direction which is perpendicular to the X direction and the Y direction.

The first output shaft 211a is extended from the center at one end of the first source 21a, and the other end of the first output shaft 211a is fixedly engaged with the transmission member 22a. The transmission member 22a includes a transmission portion 221a, an eccentric portion 223a, a base portion 225a, and a fixing rod 227a. A bottom side of the base portion 225a is recessed inward to form a groove, and a top side of the base portion 225a is fixedly connected to the center of the connecting portion 41.

A lower end of the transmission portion 221a is connected to the center of the top of the first output shaft 211a, and the eccentric portion 223a is located on the upper end of the transmission portion 221a at which is distant from a center of the transmission portion 221a. The eccentric portion 223a is accommodated in the groove of the base portion 225a. The fixing rod 227a passes through the base portion 225a and rotatably connects to an inner side wall of the shell 111. The cross-sectional area of the groove gradually increases from an end close to the fixing rod 227a to an end away from the fixing rod 227a, so that the eccentric portion 223a is capable of shaking and beating the two side walls of the groove by a large margin. In this embodiment, the transmission member 22a can also be other structures, such as a gear structure, a worm structure, a rocker structure, and so on.

When the first driving source 21a works, the transmission portion 221a is driven to rotate by the first output shaft 211a, and the eccentric portion 223a is driven to shaking back and forth in the groove, beating the sidewall of the groove along the Z direction which perpendicular to the X direction and the Y direction simultaneously, the base portion 225a is driven to rotate relative to the fixing rod 227a by the eccentric portion 223a, and then drives the connecting portion 41 to swing in the Z direction. The connecting portion 41 is thus driven to swing back and forth violently relative to the shell 111 along the Z direction, and the lateral wall 402 of the first massage member 40 is driven to swing simultaneously. Since the first massage area 43 and the second massage area 45 are formed with a wrinkle therebetween, and both the lateral wall 402 and the connecting portion 41 are made of the first material which have a large elasticity, the connecting portion 41 drives the lateral wall 402 to swing along the Z direction, as well as swing gently along the X and Y directions.

It can also be understood that the transmission member 221a drives the eccentric portion 223a to shake back and forth to beat the side wall of the groove along the Y direction, so that the connecting portion 41 shakes up and down relative to the shell 111 along the Y direction. And then the lateral wall 402 may be driven to shake up and down while moving slightly in the X and Z directions.

Alternatively, the transmission member 221a drives the eccentric portion 223a to move back and forth in the groove along the X direction, so that the connecting portion 41 moves back and forth relative to the shell 111 along the X direction, and then the lateral wall 402 can also be driven to swing back and forth while moving slightly along the Y direction and the Z direction.

Figure 12:
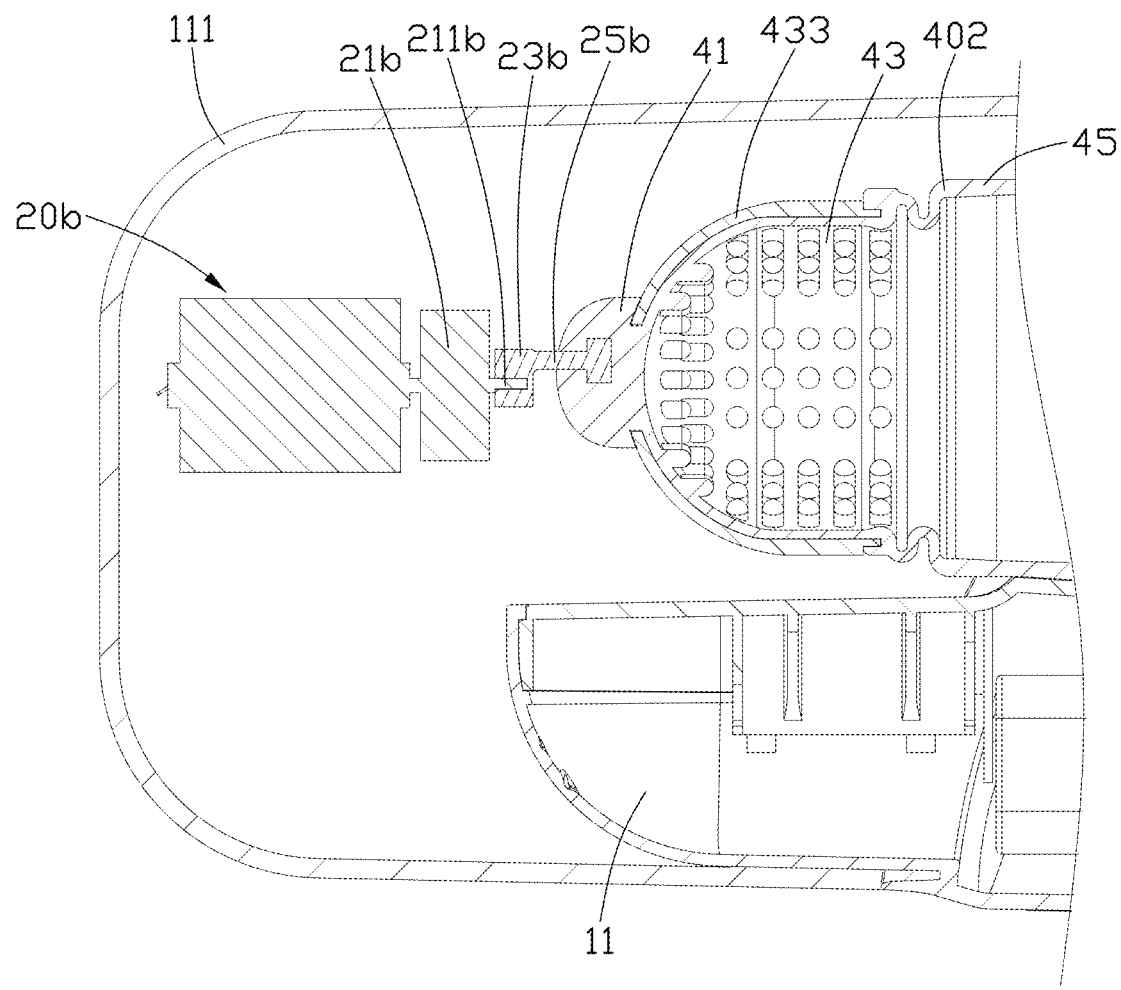
FIG. 12 is a cross-sectional view of the first driving mechanism of the sperm extractor shown in FIG. 11.

As shown in FIG. 12, the first drive mechanism 20b may be another structure, that is, the first drive mechanism 20b includes the first drive source 21b, a first output shaft 211b, a first wheel 23b, and a first eccentric portion 25b. The first output shaft 211b has two ends, one of the two ends is connected to a center of the first driving source 21b, and the other end is fixed to a center of the first wheel 23b.

One end of the first eccentric portion 25b is disposed at which is distant from a center of the first wheel 23b away from the first output shaft 211b, and the other end is inserted into a center of the connecting portion 41 to form a fixing point. Under the drive of the first driving source 21b, the first output shaft 211b drives the first rotating wheel 23b to rotate, the first wheel 23b drives the connecting portion 41 to rotate simultaneously with the first eccentric portion 25b, and the lateral wall 402 is also driven to rotate. Since the first driving source 21b rotates at a high frequency and the connecting portion 41 has no structure of limiting the movement direction, the lateral wall 402 may also move in different directions during rotation.

Third Embodiment

Figure 13:
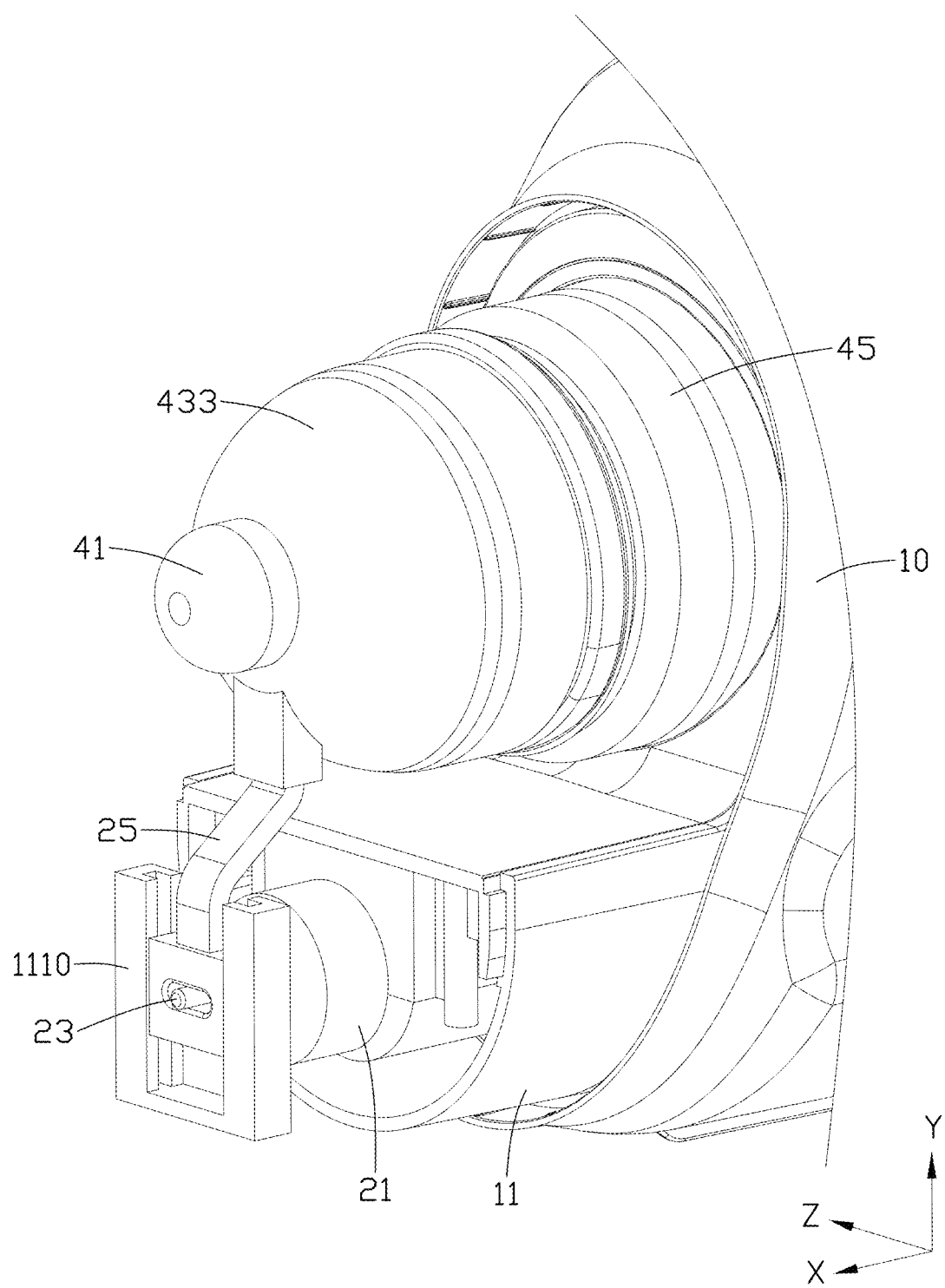
FIG. 13 is a partly perspective view showing a first driving mechanism and a limiting portion engaged with each other of a sperm extractor according to a third embodiment of the present disclosure.

As shown in FIG. 13, reference numerals same as those in Embodiment 1 continue to be used for same elements in this embodiment. A difference between this embodiment and Embodiment 1 lies in that a limiting portion 1110 is located in the shell 111 or the first driving mechanism 20, and the limiting portion is configured for restricting from moving in a linear direction for the connecting portion 41.

The limiting portion 1110 in this embodiment is located on the inner wall of the shell 111 near the connecting portion 41. The limiting portion 1110 includes two conducting bars 1110 extending in the Y direction perpendicular to the inserting direction (e.g. X direction) and the Z direction. The end of the first wheel 23 away from the first driving source 21 is slidably connected to a sliding block (not labeled), and the sliding block is slidably engaged with the conducting bars 1110 along the Y direction. The first rod 25 is fixedly connected to a top end of the sliding block, the rotation of the first wheel 23 is converted into the sliding of the sliding block.

The connecting portion 41 is connected with the first rod 25. The first rod 25 slides along the extending direction of the conducting bar 1110, drives the first massage area 43 and the second massage area 45 to shaking up and down. The first massage area 43 and the second massage area 45 are also driven to move softly in the X direction and the Z direction simultaneously.

Figure 14:
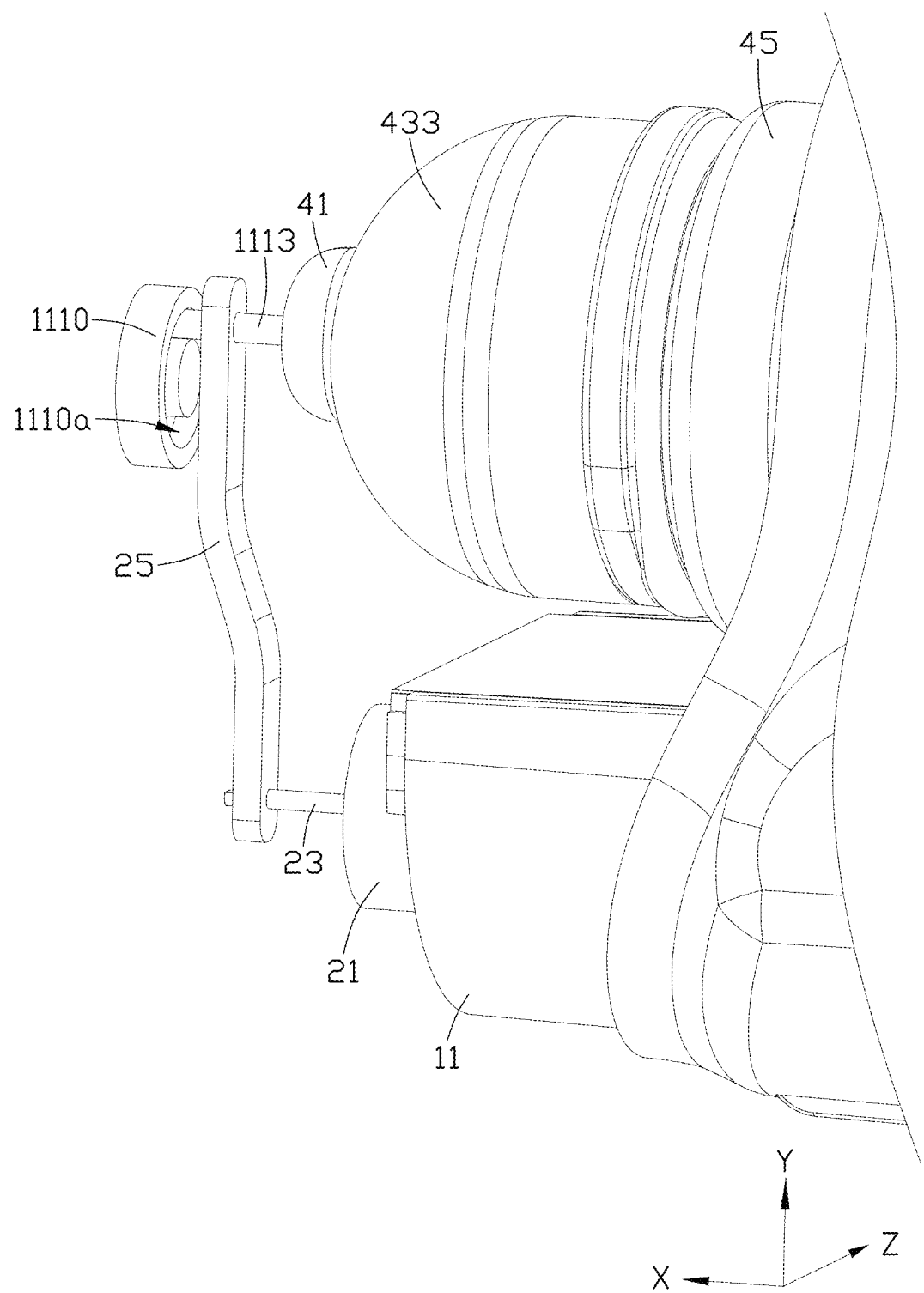
FIG. 14 is a partly perspective view of another illustrative structure of the first driving mechanism and the limiting portion shown in FIG. 13.

As shown in FIG. 14, the limiting portion 1110 may be circular-shaped and defines a limiting groove 1110a. A guide rod 1113 is movably inserted into the limiting groove 1110a. The guide rod 1113 extends along the X direction, passes through the end of the first rod 25 away from the first wheel 23 and then engages with the connecting portion 41. Under the drive of the first driving source 21, the first rod 25 is driven to move up and down along the Y direction, the guide rod 1113 is driven to move along the limiting groove 1110a, and drives the connecting portion 41 to move following the motion of the guide rod 1113. The lateral wall 402 is then driven to swing and shake simultaneously, and the lateral wall 402 can also move in multiple directions in a manner similar to circular shaking under the action of the elastic force and inertia.

It can be understood that the limiting portion 110 may be other structures, as long as the connecting portion 41 can be driven to move along a certain straight line or curved direction.

Fourth Embodiment

Figure 15:
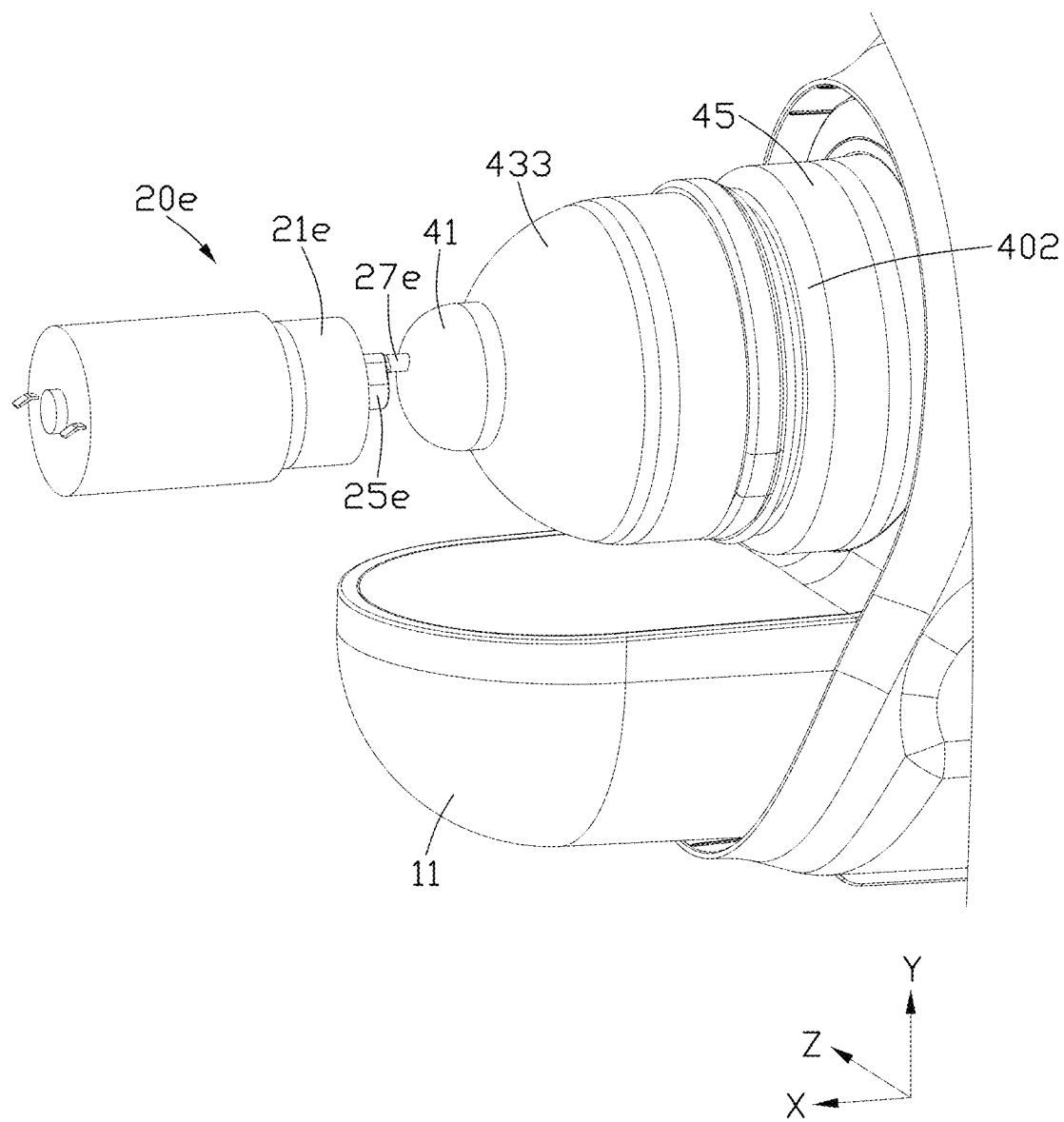
FIG. 15 is a view showing an engagement of a first driving mechanism and a connecting portion of a sperm extractor according to a fourth embodiment of the present disclosure.

As shown in FIG. 15, reference numerals same as those in Embodiment 1 continue to be used for same elements in this embodiment. A difference between this embodiment and Embodiment 1 lies in a location of the first driving mechanism 20 and a connecting position between the first driving mechanism 20 and the connecting portion 41.

The first driving mechanism 20 is fastened on the shell 111, and is arranged along the X direction which parallel to the inserting direction. The first driving mechanism 20 comprises a first drive source 21, a cam 25, and an eccentric portion 27. One end of the first drive source 21 protrudes a shaft and the shaft is connected to one side of the cam 25. The eccentric portion 27 is disposed at a location which is distant from a center of the cam 25 away from the shaft, similarly, the eccentric portion 27 is fixedly engaged with the connecting portion 41 at a position which is away from the center of the connecting portion 41. The shaft is driven to rotate by the first driving source 21, and then the cam 25 is also driven to rotate, the cam 25 drives the connecting portion 41 to move clockwise and counterclockwise at an angle, and the lateral wall 402 is driven to rotate clockwise and counterclockwise simultaneously by the connecting portion 41, and the lateral wall 402 can move in multiple directions to perform similar circular motion due to the elasticity and inertia.

Fifth Embodiment

Figure 16:
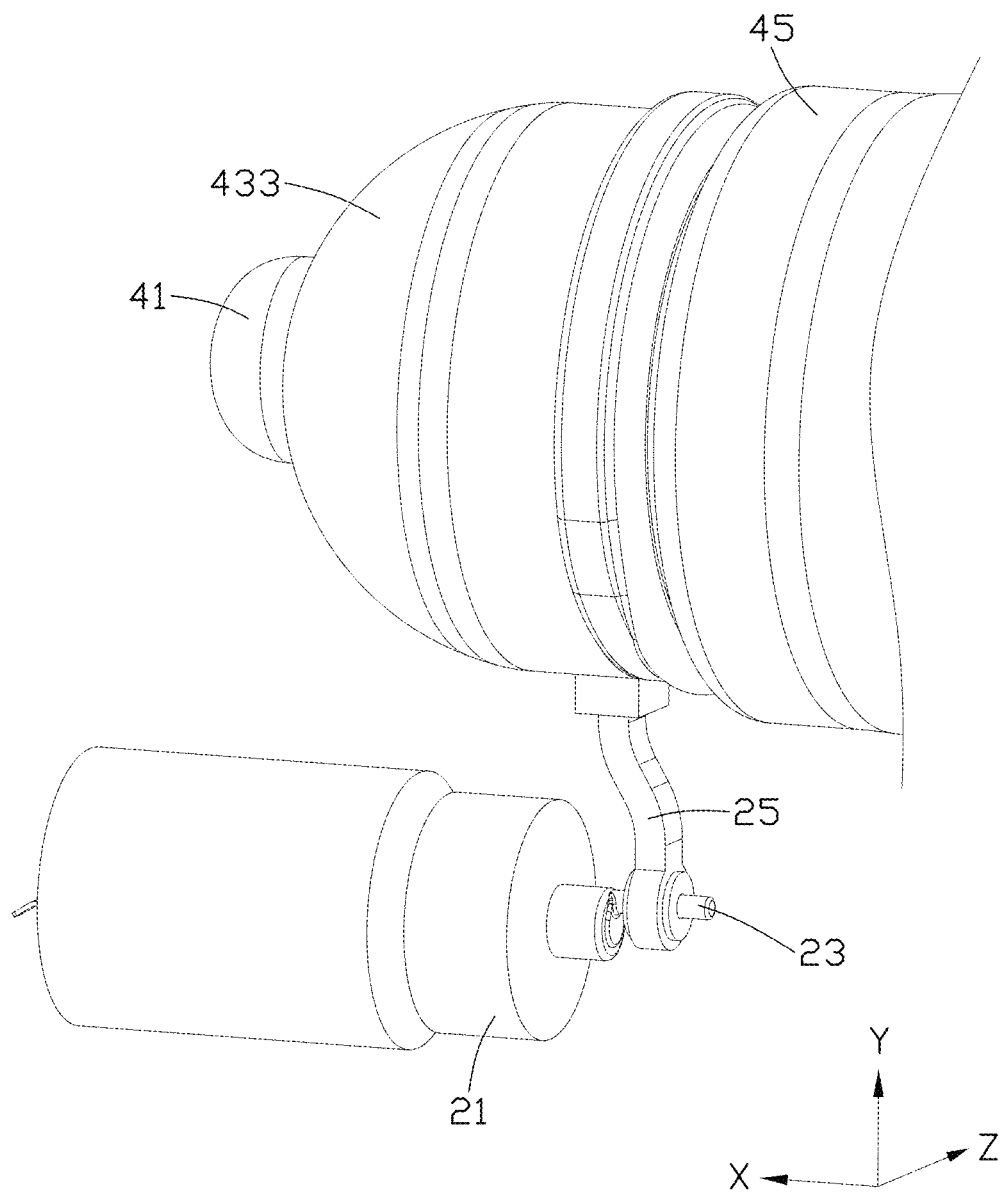
FIG. 16 is a view showing an engagement of a first rod and a first sleeve of a sperm extractor according to a fifth embodiment of the present disclosure.

As shown in FIG. 16, reference numerals same as those in Embodiment 1 continue to be used for same elements in this embodiment. A difference between this embodiment and Embodiment 1 lies in that the first rod 25 engages with an end of the first sleeve 433 without engaging with the connecting portion 41.

Under the drive of the first driving source 21, the first wheel 23 drives the first rod 25 to move up and down along the up-and-down direction (e.g. Y direction), and the first sleeve 433 is driven to move up and down by the first rod 25, so that the first massage area 43 is driven to move down and up, and the second massage area 45 is also driven to move simultaneously. Since the second massage area 45 has large elasticity and inertial force, the movement direction of the second massage area 45 is irregular, including movements similar to swinging, vibrating, shaking, rotating, and other movements in multiple directions.

Sixth Embodiment

Figure 17:
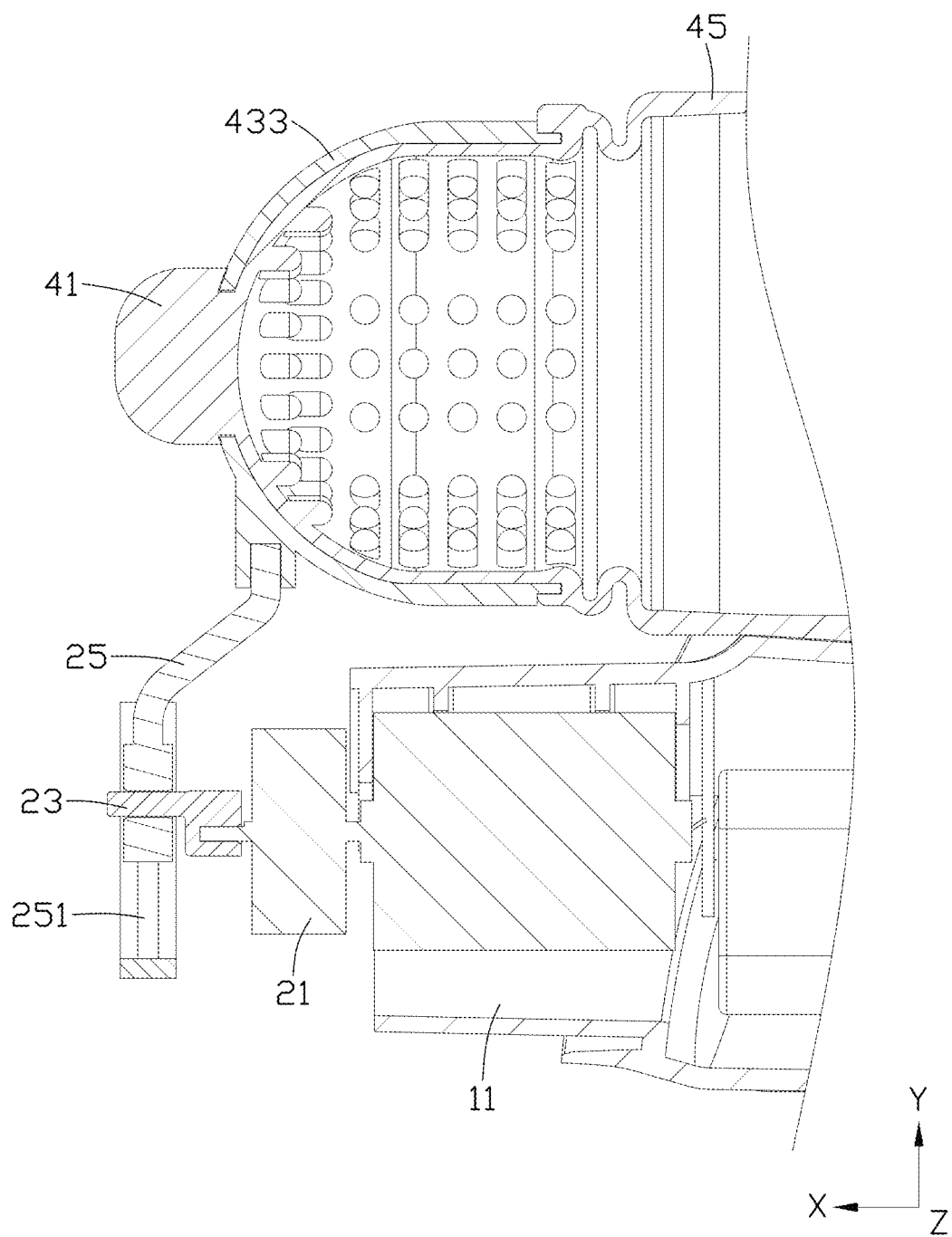
FIG. 17 is a cross-sectional view showing an engagement of a limiting member, a first driving mechanism and a first sleeve of a sperm extractor according to a sixth embodiment of the present disclosure.

As shown in FIG. 17, reference numerals same as those in Embodiment 1 continue to be used for same elements in this embodiment. A difference between this embodiment and Embodiment 1 lies in that the first rod 25 engages with an end of the first sleeve 433 near the connecting portion 41, and a limiting member 251 is installed in an end of the first rod 25 so at to limit the movement direction of the first rod 25.

The limiting member 251 is fixedly received in the first housing 11. In this embodiment, the limiting member 251 is a guide bar extending along the Y direction perpendicular to the inserting direction (e.g. X direction). Under the drive of the first driving source 21, the first rod 25 moves up and down along the extending direction of the guide bar 251, and drives the end of the first sleeve 433 to move up and down accordingly, and the end of the second massage area 45 near the sleeve 43 is driven to move up and down simultaneously. Due to the inherent elastic force of the second massage area 45 and the inertial forces during movement, the second massage area 45 also performs a circular-like motion in multiple directions.

Figure 18:
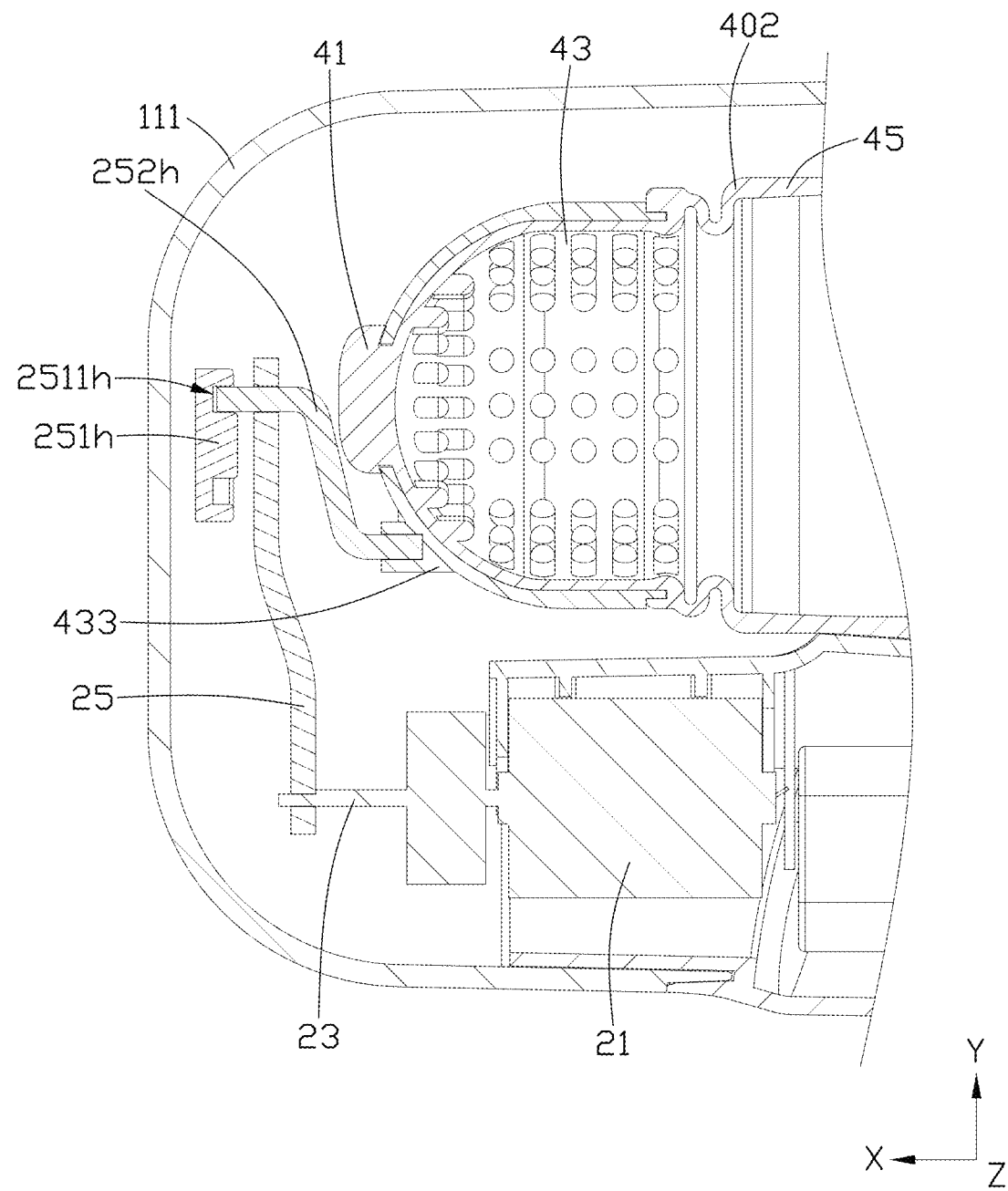
FIG. 18 is a cross-sectional view showing an engagement of another illustrative structure of the first driving mechanism, a first rod and the first sleeve of the sperm extractor according to the sixth embodiment of the present disclosure.

Refer to FIG. 18, it can be understood that the limiting member 251 can be protruded from the inner wall of the shell 111, the limiting member 251 is located corresponding to the position of the connecting portion 41.

The limiting member 251 may be circular-shaped and defined a limiting slot 251a. A guide shaft 252 is limited by the limiting slot 251a, extended along the X direction. The guide shaft 252 passes through the end of the first rod 25 away from the first wheel 23 and then engages with the first sleeve 433. Under the drive of the first driving source 21, the first rod 25 is driven to move up and down along the Y direction, the guide shaft 252 is driven to move along the limiting slot 251a, and drives the first sleeve 433 to move around the extending direction of the guide shaft 252 reciprocally, and then the lateral wall 402 is driven to move simultaneously. The lateral wall 402 can also move in multiple directions in a manner similar to circular shaking under the action of the elastic force and inertia of the movement.

Seventh Embodiment

Reference numerals same as those in Embodiment 1 continue to be used for same elements in this embodiment. A difference between this embodiment and Embodiment 1 lies in the structure of the first driving mechanism 20.

The structure of the first driving mechanism 20 in this embodiment is similar to that in embodiment 2, it can also drive the first sleeve 433 to shake along the X direction, or the Y direction, or the Z direction, or rotate.

Eighth Embodiment

Reference numerals same as those in Embodiment 1 continue to be used for same elements in this embodiment. A difference between this embodiment and Embodiment 1 lies in that the first rod 25 engages with an end of the first sleeve 433 near the connecting portion 41, and the structure of the first driving mechanism 20 is different.

Figure 19:
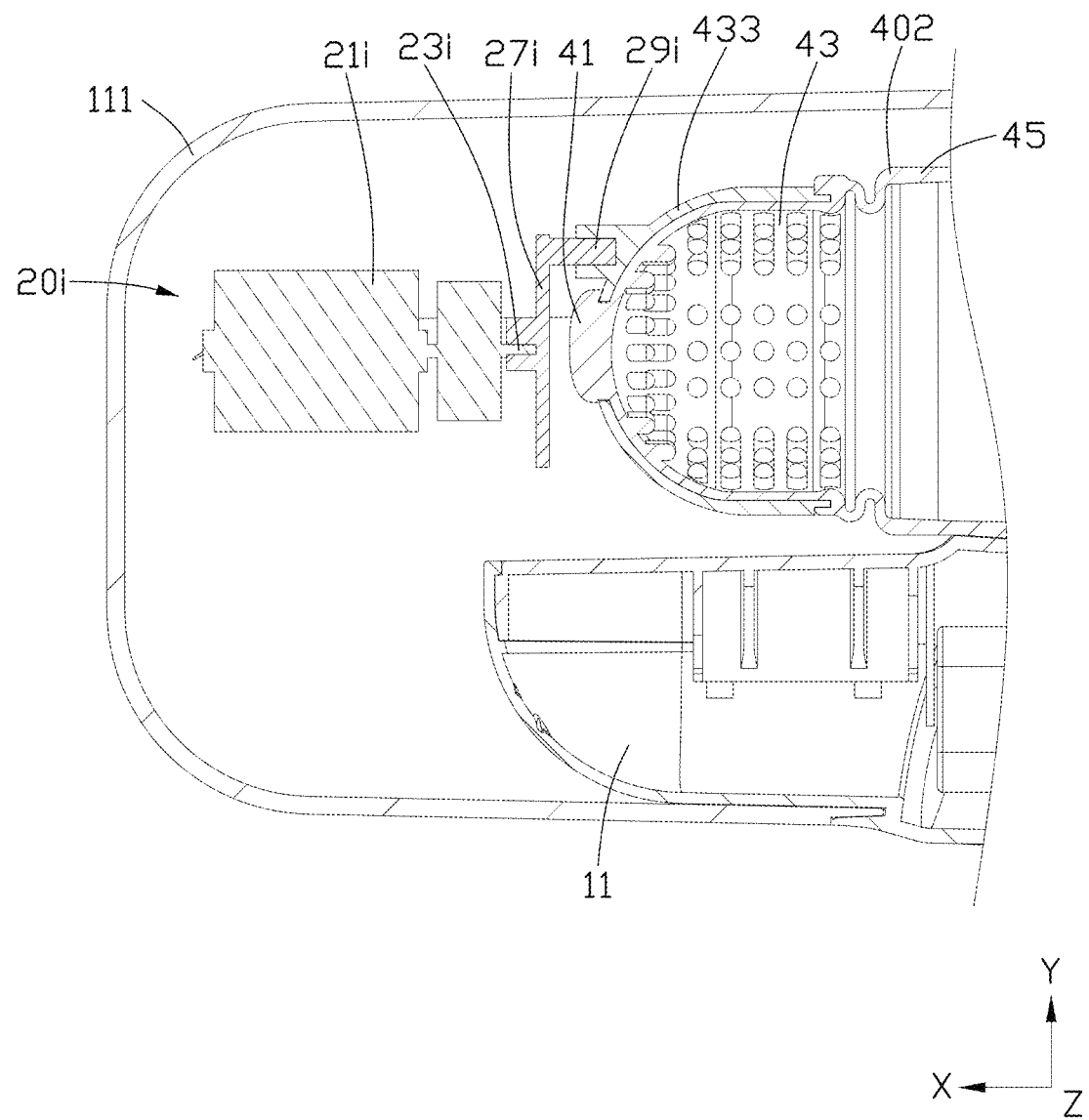
FIG. 19 is a cross-sectional view showing an engagement of a first driving mechanism and a first sleeve of a sperm extractor according to an eighth embodiment of the present disclosure.
Figure 20:
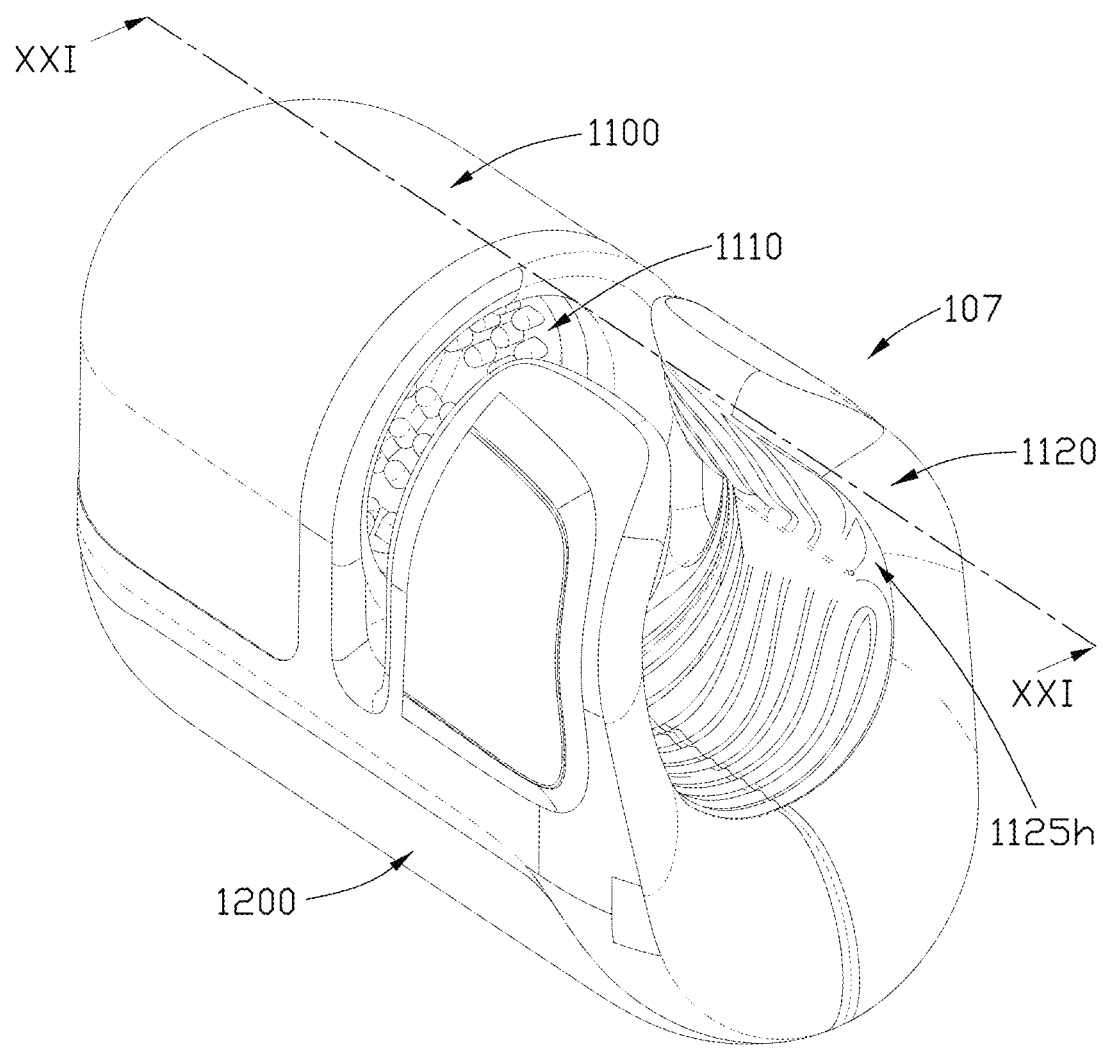
FIG. 20 is a perspective view of a sperm extractor according to a ninth embodiment of the present disclosure.
Figure 21:
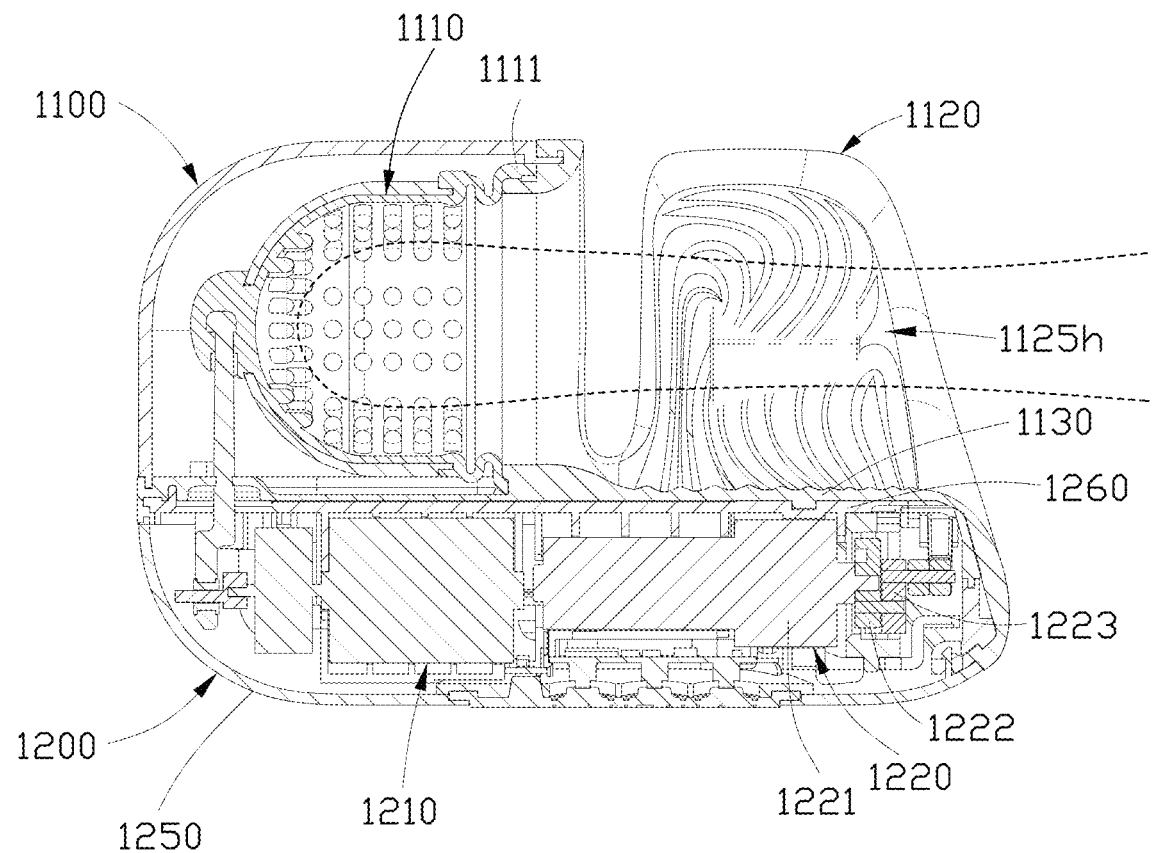
FIG. 21 is a cross-sectional view of the sperm extractor shown in FIG. 20.
Figure 22:
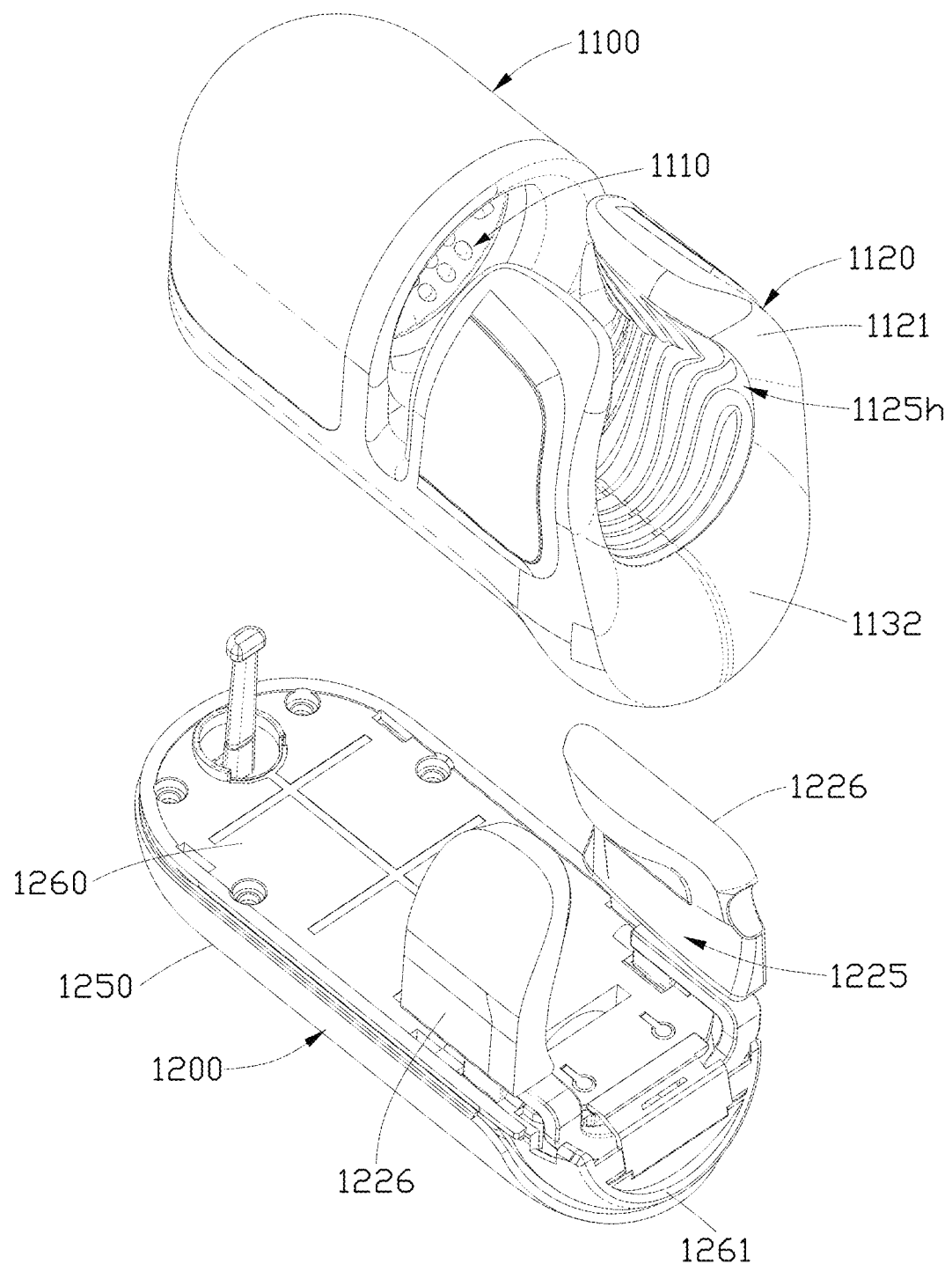
FIG. 22 is an exploded view of the sperm extractor shown in FIG. 20.
Figure 23:
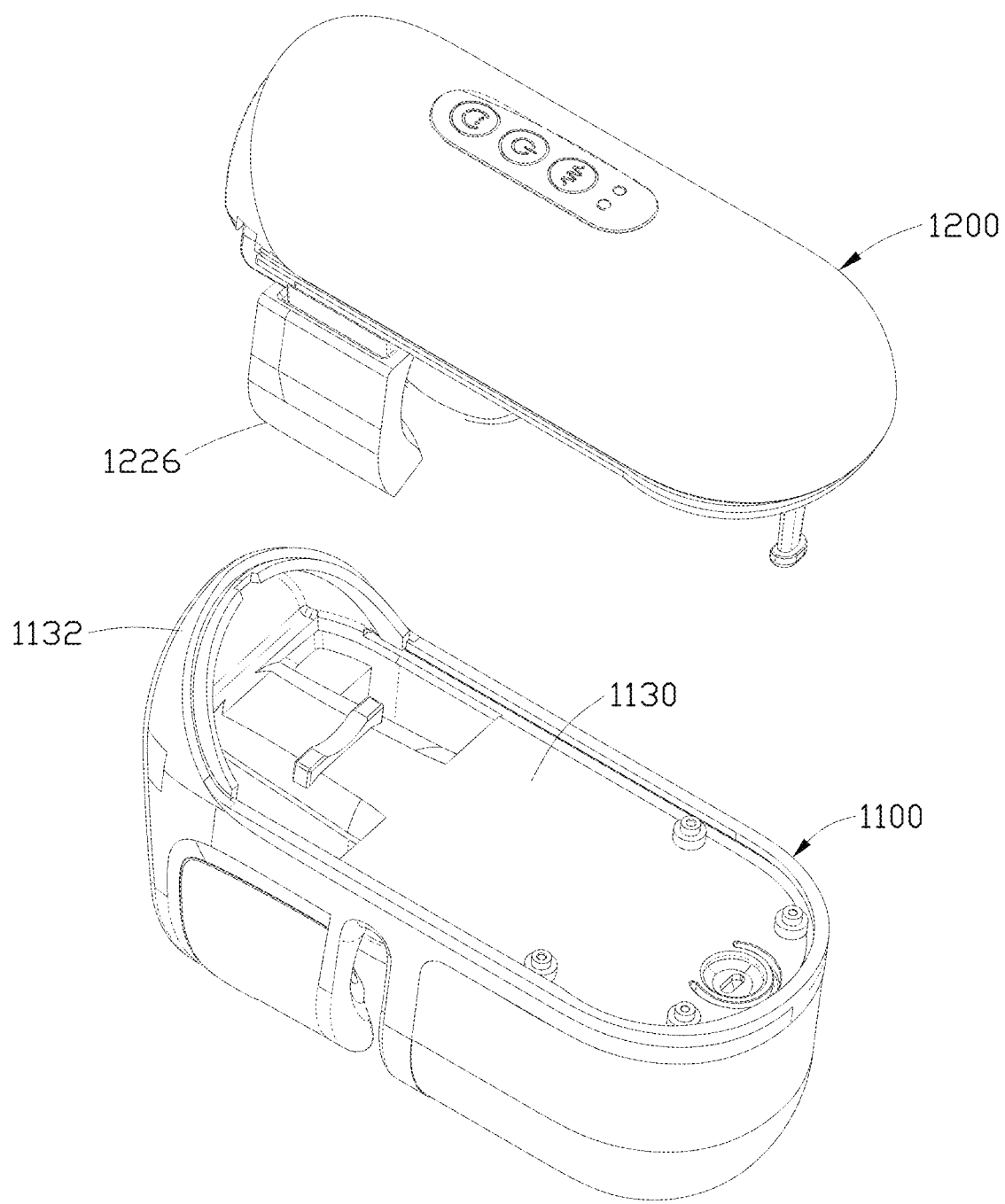
FIG. 23 is an exploded view of the sperm extractor shown in FIG. 20 showing from another view direction.
Figure 24:
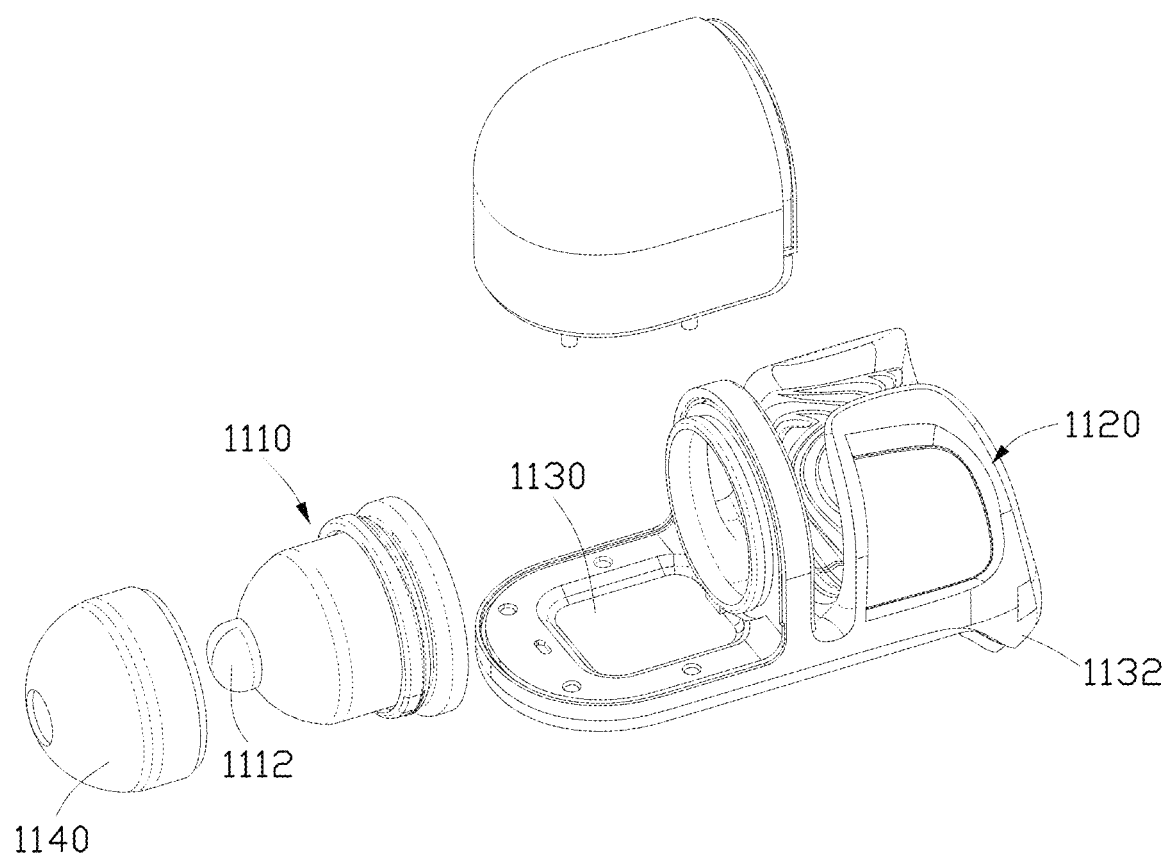
FIG. 24 is an exploded view showing a first housing of the sperm extractor shown in FIG. 22.
Figure 25:
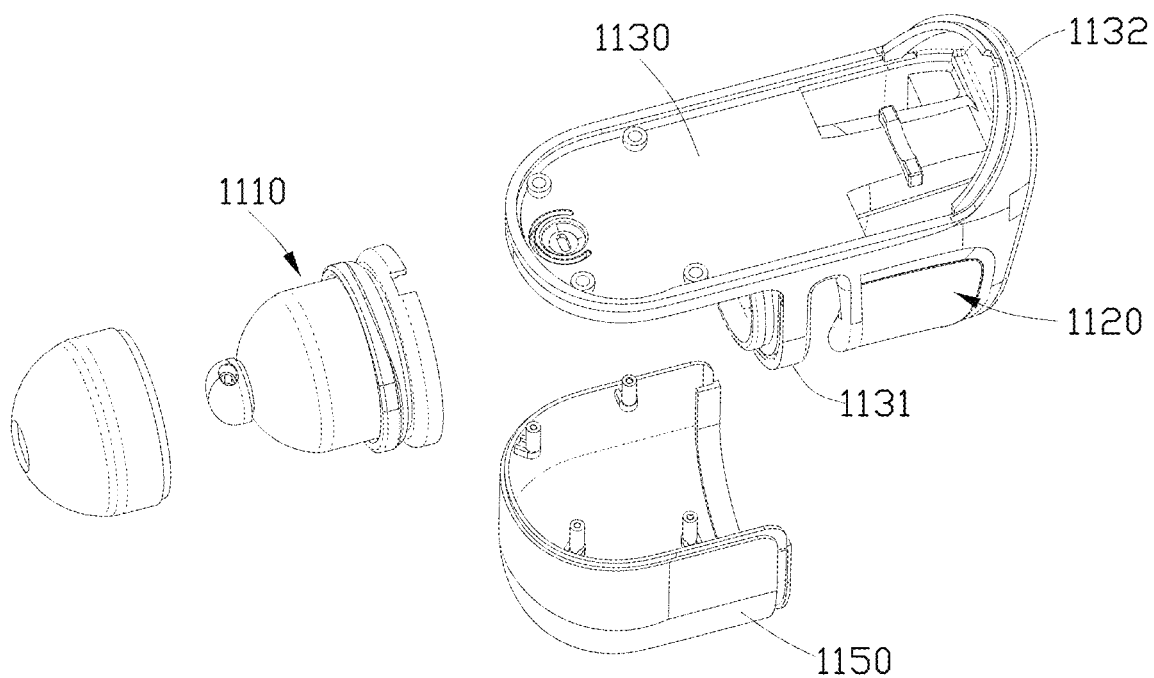
FIG. 25 is an exploded view showing the first housing of the sperm extractor shown in FIG. 22 showing from another view direction.
Figure 26:
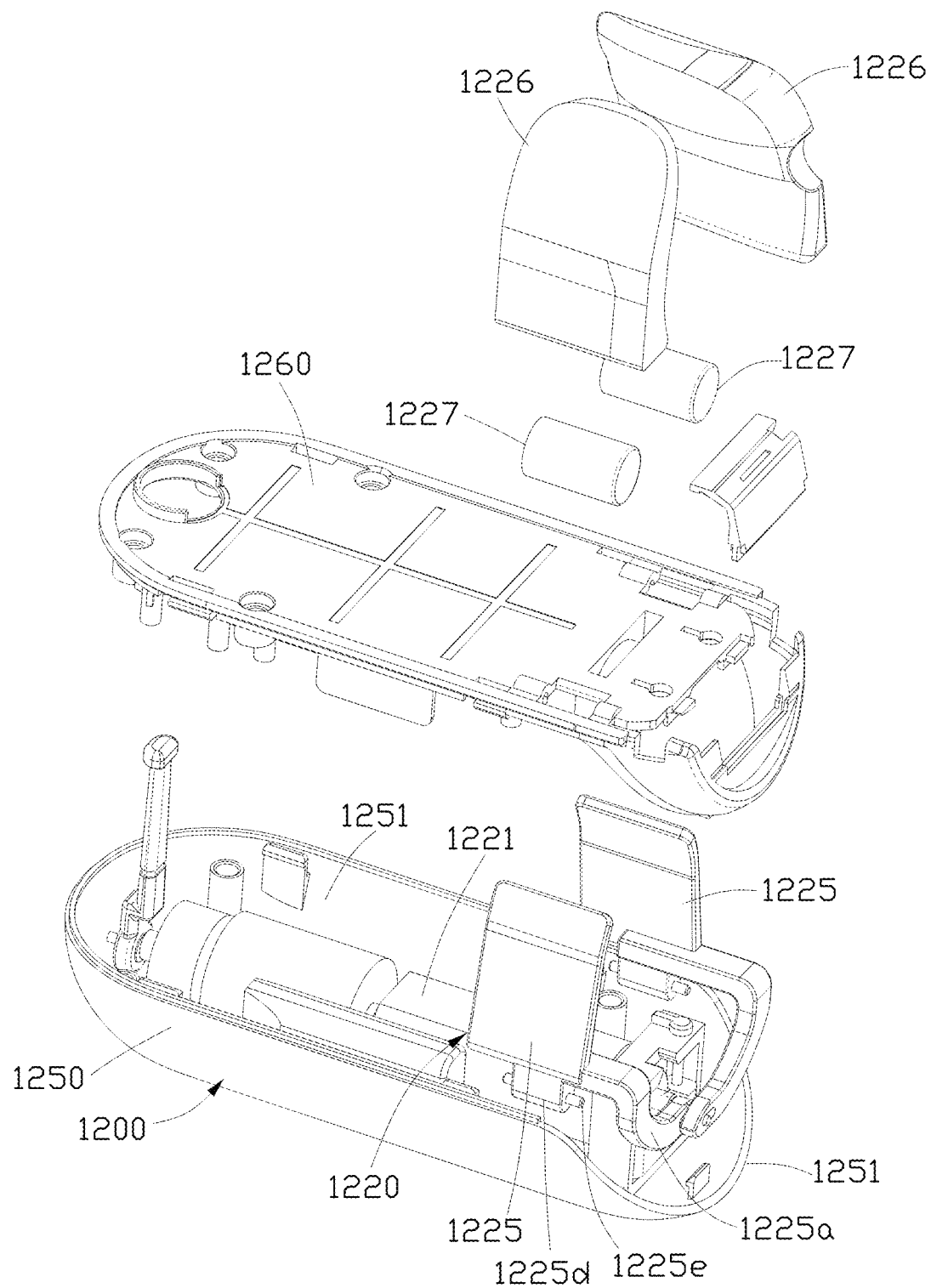
FIG. 26 is an exploded view showing a second housing of the sperm extractor shown in FIG. 22.
Figure 27:
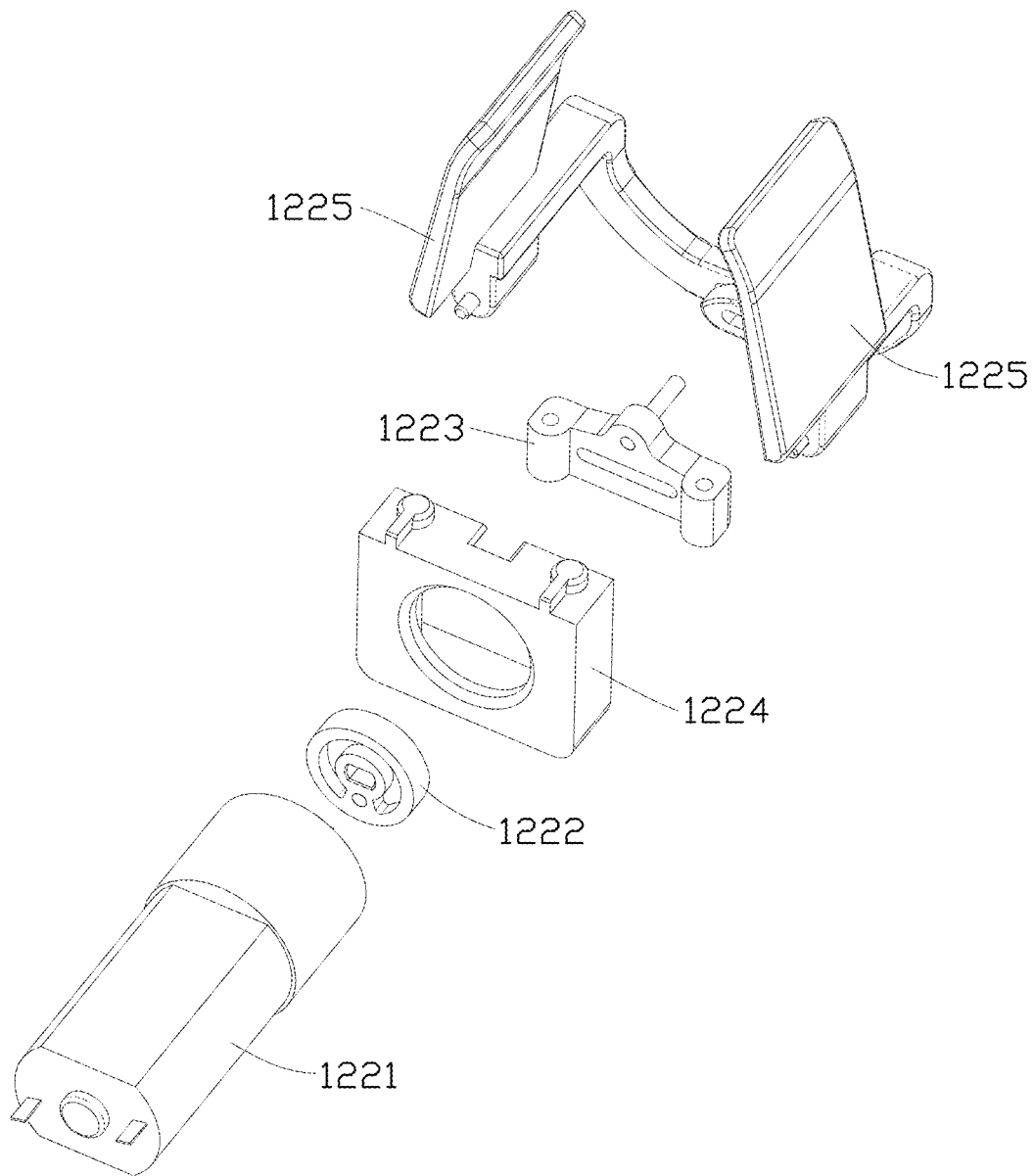
FIG. 27 is an exploded view showing a second driving unit of the sperm extractor shown in FIG. 22.
Figure 28:
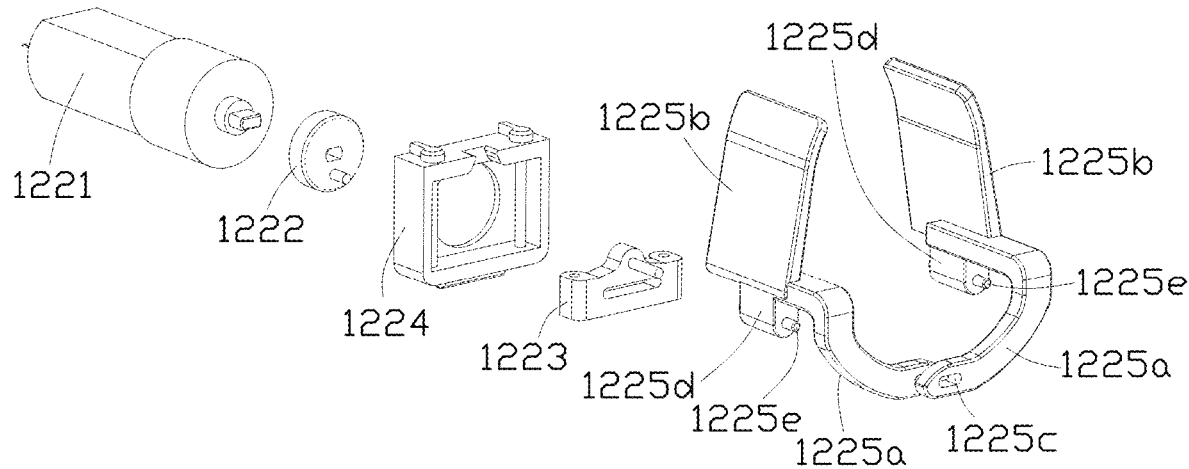
FIG. 28 is an exploded view showing the second driving unit of the sperm extractor shown in FIG. 22 showing from another view direction.

As shown in FIG. 19, the first driving mechanism 20 includes a first driving source 21, a first output shaft 23, a rotating member 27, and a protrusion 29. One end of the first output shaft 23 is fixedly connected to the first driving source 21, and the other end is connected to one end of the rotating member 27, and one side of the rotating member 27 away from the first output shaft 23 is connected to the protrusion 29. The protrusion 29 is protruded from the location which is distant from the central of the rotating member 27, and the protrusion 29 engages with one side of the first sleeve 433 near the concocting portion 41.

The first output shaft 23 is driven to rotate by the first driving source 21, the rotating member 27 is also driven to rotates clockwise and counterclockwise alternately, the protrusion 29 is driven to move and drives the first sleeve 433 to move simultaneously, and the lateral wall 402 is driven to rotate clockwise and counterclockwise alternately. Due to the elasticity of the lateral wall 402 and the inertia generated during the movement, the lateral wall 402 also moves in multiple directions to generate rotation, shaking, and swinging.

Ninth Embodiment

Refer to FIG. 20 to FIG. 28, the application No. 202420234046.9 of the entire contents of the priority document application are hereby incorporated by reference. A difference between this embodiment and Embodiment 1 lies in the structure of the first housing 1100, the second housing 1200 and the second massage module 107.

The first housing 1100 and the second housing 1200 are engaged with each other along the Y direction perpendicular to the inserting direction (e.g. X direction). The second massage module 107 comprises a second massage part 1120 and a second driving unit 1220. The second massage part 1120 includes a pair of swinging members 1225 arranged opposite to each other, the pair of swinging members 1225 are arc structure and cooperatively to form a second inserting space 1125h to receive a portion of penis.

One end of the pair of swinging members 1225 intersect with each other, while the other end of that is capable of moving close to or away from each other under the drive of the second driving unit 1220, thereby compressing or releasing the penis of the massage space 60a.

The first housing 1100 includes a first support plate 1130, and a first inclined portion 1132 protrudes from an end of the first support plate 1130 adjacent to the second massage part 1120 toward the second housing 1200.

The second housing 1200 includes a bottom housing 1250 and a second support plate 1260 covering the bottom housing 1250. The bottom housing 1250 and the second support plate 1260 are cooperatively to define a receiving cavity 1251, and the receiving cavity 1251 is used for receiving the first driving unit 1210 and the second driving unit 1220. A second inclined portion 1261 also protrudes from one end of the second support plate 1260, and the first inclined portion 1132 and the second inclined portion 1261 are engaged with each other.

An inclined notch 1251 with arc-shaped is defined at one end of the bottom housing 1250 to be engaged with the second inclined portion 1261.

The second driving unit 1220 includes a second driving source 1221, a second wheel 1222, a sliding block 1223, a bracket 1224. The second wheel 1222 is connected to the second driving source 1221, the sliding block 1223 is connected to the second wheel 1222, the bracket 1224 is configured for supporting the sliding block 1223, and the sliding block 1223 is engaged with the pair of swinging members 1225. The second driving source 1221, the second wheel 1222, the sliding block 1223, and the bracket 1224 are accommodated within the receiving cavity 1251, and a portion of the pair of swinging members 1225 is protruded from the second support plate 1260.

Each swinging member 1225 includes an arm portion 1225a and a swinging portion 1225b connected to one end of the arm portion 1225a. A connecting hole 1225c is defined at one end of the arm portion 1225a away from the swinging portion 1225b, and a transmission shaft 1223c of the sliding block 1223 is slidably connected to the connecting hole 1225c. A mounting post 1225d protrudes from one end of the swinging portion 1225b adjacent to the arm portion 1225a, and the mounting post 1225d is rotatably connected to the second housing 1200 through a rotating shaft 1225e.

When the second driving source 1221 works, the second wheel 1222 rotates and drives the sliding block 1223 to slide up and down along the extending direction of the bracket 1224, and the transmission shaft 1223c on the sliding block 1223 drives the pair of swinging members 1225 to rotate around the corresponding rotating shaft 1225e respectively, so that each swinging member 1225 swings toward or away from each other.

A finger cover 1226 is covered on the outer wall of the pair of swinging portion 1225b, and a vibration is received in the finger cover 1226 adjacent to an end of the swinging portion 1225b, so that a vibrating massage is performed while the pair of swinging members 1225 clamp and massage the penis.

The invention claimed is:

1. A stimulating device comprising:
a first massage member configured for massaging a penis, the first massage member defining a first inserting space which is configured for receiving the penis, the first inserting space defining an inserting direction along which the penis is insertable into the first inserting space, the first massage member including a first end, a second end opposite to the first end, and a lateral wall between the first end and the second end, the lateral wall surrounding and defining the first inserting space, the lateral wall including a first massage portion configured for massaging a glans of the penis received in the first inserting space; and,
a first driving mechanism configured for driving the first massage member,
wherein a connecting portion is formed at one of the first end and the second end of the first massage member, the first driving mechanism is coupled to the connecting portion and drives the connecting portion to move in a virtual plane perpendicular to the inserting direction;
the first massage portion is driven to move by the connecting portion, an entirety of the first massage portion is deviated toward a first direction at a first time, the first direction intersects with the inserting direction, the entirety of the first massage portion deviates toward a second direction at a second time, the second direction intersects with the inserting direction, the first direction is opposite to the second direction, the first time is before the second time.

2. The stimulating device according to claim 1, wherein the connecting portion is driven to reciprocatively move along the first direction and the second direction, and the lateral wall is driven to swing simultaneously with the connection portion.

3. The stimulating device according to claim 2, wherein the first driving mechanism further includes a driving member and a transmission member, a rod, and a first connecting member,
the first connecting member is configured for connecting with the connecting portion,
an end of the transmission member connects to the driving member, another end of the transmission member engages with an end of the rod,
the first connecting member extends from an end of the rod away from the transmission member,
the transmission member is configured for converting the rotation of the driving member to the linear motion of the first connecting member,
the driving member and the transmission member are connected along a direction parallel to the inserting direction, while the rod extends in an extending direction perpendicular to the inserting direction,
when the rod is driven to move along the extending direction under the drive of the driving member, the connecting portion is driven to reciprocatively move at the extending direction.

4. The stimulating device according to claim 3, wherein a moving amplitude of the connecting portion in the first direction is larger than a moving amplitude of the connecting portion in the second direction.

5. The stimulating device according to claim 1, further comprising:
a cover covered on an outer surface of the lateral wall and movable together with the connecting portion;

Wherein, the cover is made of a first material, the lateral wall is made of a second material, the hardness of the first material is larger than that of the second material.

6. The stimulating device according to claim 1, wherein the first driving mechanism comprises a rotating shaft engages with the connecting portion, the rotating shaft extends along a direction parallel to the inserting direction,
the connecting portion is driven to be movable in an annular track in the virtual plane.

7. The stimulating device according to claim 6, wherein the first driving mechanism is located perpendicular to the inserting direction of the penis, and the first driving mechanism also comprises a driving portion and a transmission portion, an end of the transmission portion connects to the driving portion, and the shaft is protruded from a location which is distant from the center of the transmission portion away from the driving portion.

8. The stimulating device according to claim 6, wherein the first driving mechanism further comprises a driving portion and a first rod, the first rod extends along an extending direction perpendicular to the inserting direction,
a limiting portion is engageable with the first rod to limit the movement of the first rod in directions other than the extending direction of the first rod.

9. The stimulating device according to claim 1, wherein, the lateral wall forms an extensible portion which is deformable to extend and recover in the inserting direction.

10. The stimulating device according to claim 1, further comprising
a second massage member, configured to stimulate the penis,
the second massage member arranging in a side of the first massage member away from the connecting portion,
the second massage member defining a second inserting space to receive a portion of the penis,
the second inserting space is air communicated with the first inserting space,
a second driving mechanism, configured to drive the second massage member to move in a third direction,
wherein the third direction is intersected with the inserting direction, the first direction and the second direction.

11. A stimulating device comprising:
a housing,
a first stimulating member attached to the housing and configured for stimulating a front portion of a penis, the first stimulating member including a fastened end, a moveable end, and a main body between the fastened end and a moveable end, the fastened end detachably coupled to the housing, the main body configured for receiving and surrounding the front portion of the penis, the main body defining a first inserting space configured for the penis to be inserted along an insertion direction; and,
a first driving mechanism coupled to one of the moveable end and the main body, the first driving mechanism configured for driving the main body to swing away from the insertion direction of the penis;
a second stimulating member attached to the housing and configured for stimulating a rear portion of a penis, wherein the second stimulating member is separated from the first stimulating member, and the first and the second stimulating members are independently controlled.

12. The stimulating device according to claim 11, wherein,
the main body forms an enhance massage area with a first massage intensity and a non-enhance massage area with a second massage intensity,
the enhance massage area is located between the movable end and the non-enhance massage area,
the first massage intensity is stronger than the second massage intensity.

13. The stimulating device according to claim 12, wherein,
a plurality of protrusions are protruded from an inner surface of the first massage area for contacting with the penis.

14. The stimulating device according to claim 11, further comprising:
a recess inwards from an outer surface of the first stimulating member at a location between the fastened end and the main body.

15. The stimulating device according to claim 11, wherein,
the main body is at least swingable in opposite vertical directions when the main body is disposed in a horizontal direction.

16. The stimulating device according to claim 11, wherein,
the movable end is a closed end, the fasten end defines an opening for allowing the penis to be inserted into the first inserting space.

17. The stimulating device according to claim 11, wherein,
the second stimulating member has a stimulating mode different to the first stimulating member,
the second stimulating member is movable in the inserting direction, the first stimulating member is unmovable in the inserting direction.

18. The stimulating device according to claim 17, wherein,
the second stimulating member comprises a sliding guide and a massage piece slidably connected to the sliding guide;
the massage piece has a hollowed structure defining a second inserting space for inserting the penis; and the massage piece is driven to slide reciprocally to toward or away from the first massage member.

19. A stimulating device, comprising:
a housing;
a deformable member made by a first material, the deformable member defining a space for receiving at least a portion of a penis, the deformable member including a connecting portion connected to the housing and a stimulating portion extending from the connecting portion and surrounding the space for stimulating the portion of the penis in the space; and,
a nondeformable member made by a second material which has a hardness higher than that of the first material, the nondeformable member is attached to the deformable member and movable together with the deformable member.

20. The stimulating device according to claim 19, wherein,
the nondeformable member is a sleeve sleeved on the stimulating portion of the deformable member, each of the sleeve and the stimulating portion is movable in a virtual plane perpendicular to an insertion direction of the penis.

* * * * *